US012797556B2

(12) United States Patent
Hanafusa et al.

(10) Patent No.: US 12,797,556 B2
(45) Date of Patent: Nov. 17, 2026

(54) NEEDLE ASSEMBLY

(71) Applicants: IZUMI INC., Osaka (JP); ASAHI POLYSLIDER COMPANY, LIMITED, Osaka (JP)

(72) Inventors: Hiroshi Hanafusa, Maniwa (JP); Kazuharu Seki, Tokyo (JP)

(73) Assignees: IZUMI INC., Osaka (JP); ASAHI POLYSLIDER COMPANY, LIMITED, Osaka (JP)

( * ) Notice: Subject to any disclaimer, the term of this patent is extended or adjusted under 35 U.S.C. 154(b) by 494 days.

(21) Appl. No.: 18/553,219

(22) PCT Filed: Mar. 30, 2022

(86) PCT No.: PCT/JP2022/016267
§ 371 (c)(1),
(2) Date: Sep. 29, 2023

(87) PCT Pub. No.: WO2022/210964
PCT Pub. Date: Oct. 6, 2022

(65) Prior Publication Data
US 2024/0181172 A1 Jun. 6, 2024

(30) Foreign Application Priority Data
Mar. 31, 2021 (JP) ................................ 2021-061217

(51) Int. Cl.
*A61M 5/32* (2006.01)

(52) U.S. Cl.
CPC .......... *A61M 5/326* (2013.01); *A61M 5/3243* (2013.01); *A61M 2005/3254* (2013.01); *A61M 2005/3267* (2013.01)

(58) Field of Classification Search
CPC .. A61M 5/326; A61M 5/3243; A61M 5/3202; A61M 5/3271; A61M 5/3216;
(Continued)

(56) References Cited

U.S. PATENT DOCUMENTS 5,873,856 A * 2/1999 Hjertman ................ A61M 5/46 604/117
12,274,873 B1 * 4/2025 Hee-Hanson ........... A61M 5/20
(Continued)

FOREIGN PATENT DOCUMENTS

EP 3034118 6/2016
JP 2003-534105 11/2003
(Continued)

OTHER PUBLICATIONS

International Search Report and Written Opinion for International (PCT) Patent Application No. PCT/JP2022/016267, dated Jun. 14, 2022, 10 pages.

*Primary Examiner* — William H Rodriguez
(74) *Attorney, Agent, or Firm* — Sheridan Ross P.C.

(57) ABSTRACT

A needle assembly comprises a needle support portion in which a hollow needle through which a medicinal solution can flow is supported, a movable needle cover portion that is movable in an opening portion of a casing such that an injection-side end portion of the medicinal solution of the needle protrudes outward in use, a tubular portion arranged on the needle support portion and partially abuttable with the movable needle cover portion, and a biasing portion configured to bias the movable needle cover portion in a direction opposite to one direction along with movement of the movable needle cover portion in the one direction. The needle support portion, the movable needle cover portion, the tubular portion, and the biasing portion are at least partially accommodated in the casing having the opening portion.

15 Claims, 25 Drawing Sheets

(58) Field of Classification Search
CPC .. A61M 2005/3254; A61M 2005/3267; A61M 2005/3247; A61M 2005/583; A61M 2005/3217
See application file for complete search history.

(56) References Cited

U.S. PATENT DOCUMENTS

| | | | | |
|---|---|---|---|---|
| 12,377,216 | B1 * | 8/2025 | Wu | A61M 5/31525 |
| 12,377,224 | B1 * | 8/2025 | Vasiev | A61M 5/2033 |
| 2002/0004648 | A1 | 1/2002 | Larsen et al. | |
| 2003/0120209 | A1 | 6/2003 | Jensen et al. | |
| 2006/0189933 | A1 | 8/2006 | Alheidt et al. | |
| 2009/0299295 | A1 * | 12/2009 | Rubinstein | A61M 5/326 604/198 |
| 2015/0190586 | A1 | 7/2015 | Takemoto | |
| 2018/0064883 | A1 * | 3/2018 | Calvert | A61M 5/3213 |
| 2018/0214639 | A1 | 8/2018 | Takemoto | |
| 2021/0085884 | A1 * | 3/2021 | Liniger | A61M 5/31501 |
| 2021/0093799 | A1 | 4/2021 | Perot et al. | |
| 2021/0283344 | A1 * | 9/2021 | Egan | A61M 5/24 |
| 2022/0016346 | A1 * | 1/2022 | Miley | A61M 5/31576 |
| 2022/0134019 | A1 * | 5/2022 | Besson | A61M 5/3129 604/198 |
| 2022/0176045 | A1 * | 6/2022 | Allegretti | A61M 5/3245 |
| 2022/0233783 | A1 | 7/2022 | Bruns et al. | |
| 2022/0305204 | A1 * | 9/2022 | Ekman | A61M 5/3202 |
| 2022/0347392 | A1 * | 11/2022 | Zhang | A61M 5/3272 |
| 2023/0201480 | A1 * | 6/2023 | Fiard | A61M 5/3245 604/198 |
| 2023/0330340 | A1 * | 10/2023 | Zhang | A61M 5/1626 |
| 2023/0330350 | A1 * | 10/2023 | Sun | A61M 5/3202 |
| 2025/0001084 | A1 * | 1/2025 | Matsumoto | A61M 5/3286 |
| 2025/0001098 | A1 * | 1/2025 | Matsumoto | A61M 5/31 |
| 2025/0025638 | A1 * | 1/2025 | Lent | A61M 5/2033 |
| 2025/0144315 | A1 * | 5/2025 | Karlsson | A61M 5/3202 |

FOREIGN PATENT DOCUMENTS

| | | |
|---|---|---|
| JP | 4738422 | 8/2008 |
| WO | WO 2019/158549 | 8/2019 |
| WO | WO 2020/229706 | 11/2020 |

* cited by examiner

NEEDLE ASSEMBLY

CROSS REFERENCE TO RELATED APPLICATIONS

This application is a national stage application under 35 U.S.C. 371 and claims the benefit of PCT Application No. PCT/JP2022/016267 having an international filing date of 30 Mar. 2022, which designated the United States, and which PCT application claimed the benefit of Japan Patent Application No. 2021-061217 filed 31 Mar. 2021, the contents of each of which are incorporated herein by reference in their entireties.

TECHNICAL FIELD

The present disclosure relates to a needle assembly. Specifically, the present disclosure relates to a needle assembly that includes a hollow needle through which a medicinal solution can flow and is replaceably attached to a pen injector including the medicinal solution therein.

BACKGROUND ART

In recent years, it is said that the number of diabetic patients in the world will further increase in the future. Specifically, the number of diabetic patients in the world is about 400 million or more at present, and is said to increase to about 700 million after about 30 years. In order to treat diabetes, it is necessary to maintain the homeostasis of blood glucose levels, and insulin administration is essential for this purpose.

As an insulin administration method, for example, a method of using a combination of a pen injector including an insulin solution therein and a needle assembly including a hollow needle through which the medicinal solution can flow is known. According to this method, the needle assembly is attached to the pen injector, and insulin is administered after puncturing a patient or the like with the hollow needle.

PRIOR ART DOCUMENT

Patent Document

Patent Document 1: JP-B2-4738422

SUMMARY OF THE INVENTION

Problems to be Solved by the Invention

In an aspect in which the above pen injector and needle assembly are used in combination, safety protection of the hollow needle after puncturing the patient or the like and administering the medicinal solution such as insulin is required. In particular, from the viewpoint of preventing a medical worker from being mistakenly pierced with a used hollow needle attached with blood after the medicinal solution is administered to the patient or the like, the need for safety protection of the hollow needle is higher.

In this regard, it is not easy for the medical worker to cap the used hollow needle by himself/herself using a needle cover portion in daily work. Therefore, it is necessary that the hollow needle can be automatically capped. In addition, it is necessary to avoid the used hollow needle from protruding again from the needle cover portion. Furthermore, since the hollow needle attached to the pen injector is generally a replaceable disposable type, it may be necessary to have a simple structure that is less costly.

In view of the foregoing, it is an object of the present disclosure to enable provision of an automatic cap of a hollow needle, prevention of re-protrusion of the hollow needle, and a needle assembly capable of providing a simple structure.

Solutions to the Problems

In order to solve the above problems, in an embodiment of the present disclosure, there is provided a needle assembly comprising: a needle support portion in which a hollow needle through which a medicinal solution can flow is supported; a movable needle cover portion that is movable in an opening portion of a casing such that an injection-side end portion of the medicinal solution of the needle protrudes outward in use; a tubular portion arranged on the needle support portion and partially abuttable with the movable needle cover portion; and a biasing portion configured to bias the movable needle cover portion in a direction opposite to one direction along with movement of the movable needle cover portion in the one direction, the needle support portion, the movable needle cover portion, the tubular portion, and the biasing portion being each configured to be at least partially accommodated in the casing having the opening portion, in which at least the movable needle cover portion abuts on the tubular portion by the movement of the movable needle cover portion in the one direction to axially rotate from a predetermined position before movement to another position, so that the movable needle cover portion after the axial rotation is movable in the opposite direction by the biasing portion, and in which the movable needle cover portion after the axial rotation, which has completed the movement in the opposite direction, can be locked to the casing.

Effects of the Invention

According to the needle assembly according to the embodiment of the present disclosure, it is possible to provide the automatic cap of the hollow needle, the prevention of re-protrusion of the hollow needle, and the simple structure.

DETAILED DESCRIPTION

Hereinafter, a needle assembly according to an embodiment of the present disclosure will be described with reference to the drawings.

The present inventors have intensively studied a solution for enabling provision of an automatic cap of a hollow needle, prevention of re-protrusion of the hollow needle, and a simple structure, and as a result, have provided a needle assembly according to the embodiment of the present disclosure.

Figure 1A:
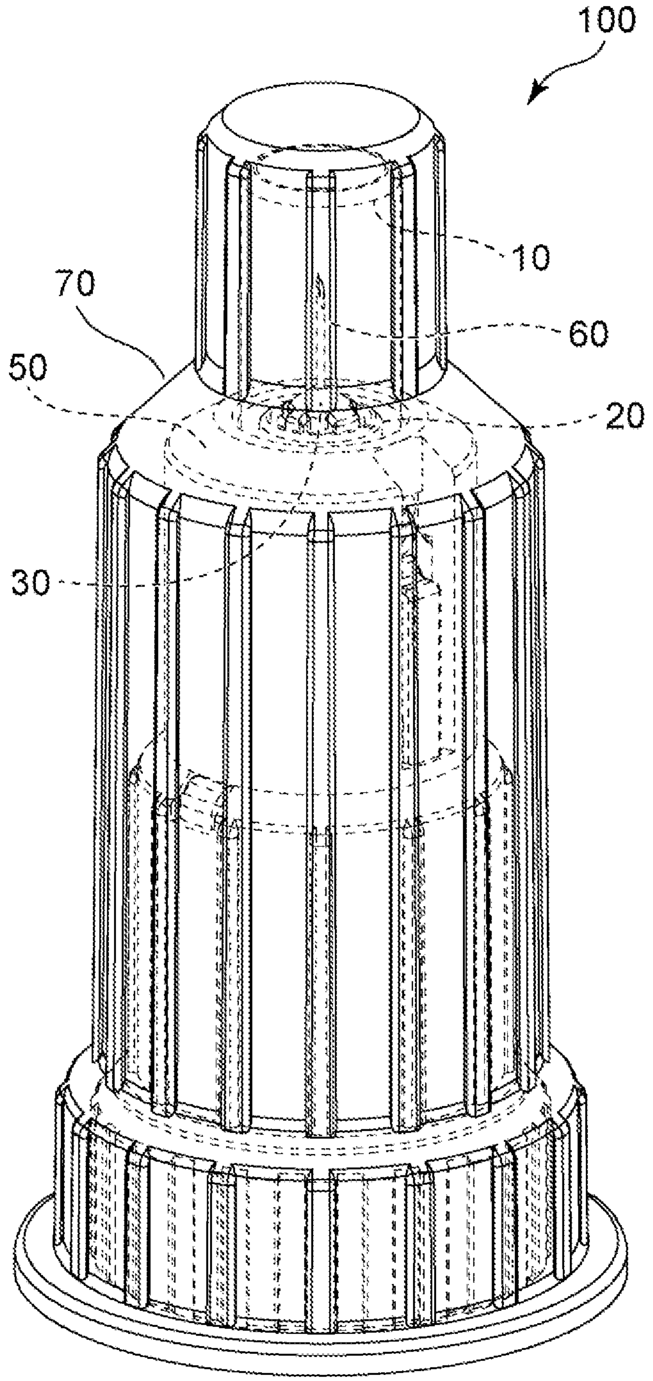
FIG. 1A is a perspective view schematically showing a needle assembly (with an overall cover) according to an embodiment of the present disclosure.
Figure 1B:
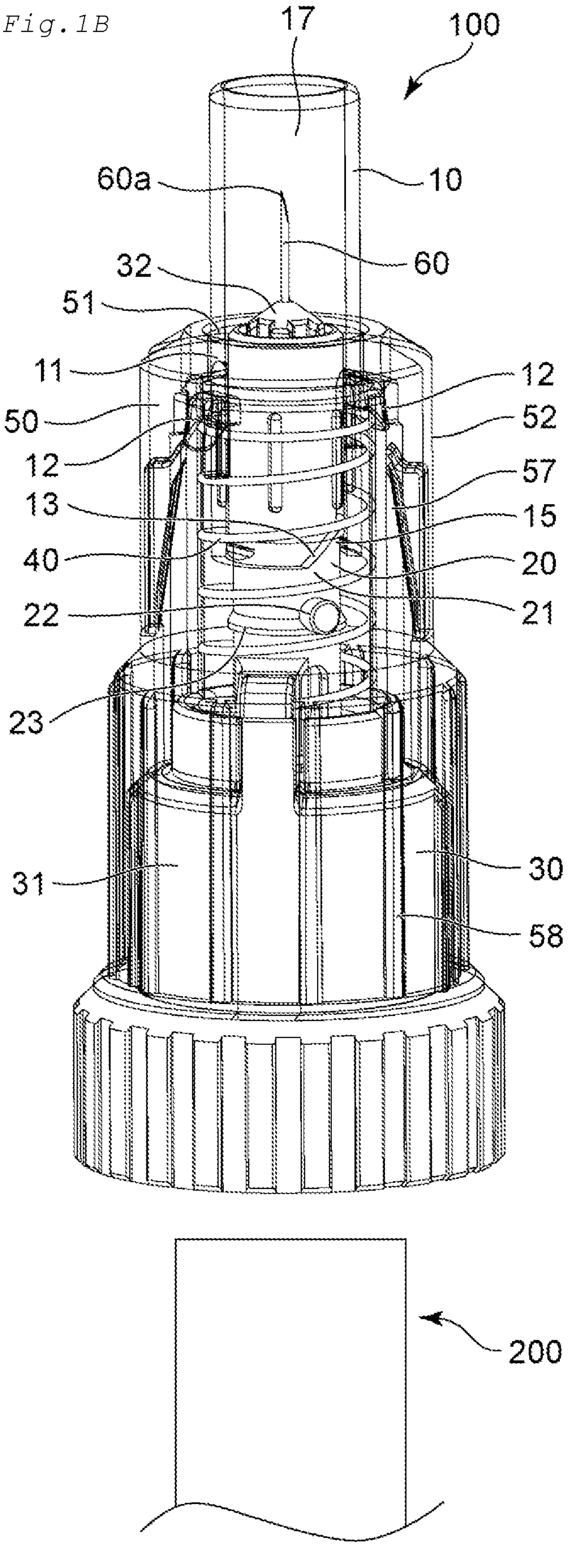
FIG. 1B is a perspective view schematically showing the needle assembly (without the overall cover) according to the embodiment of the present disclosure.
Figure 2:
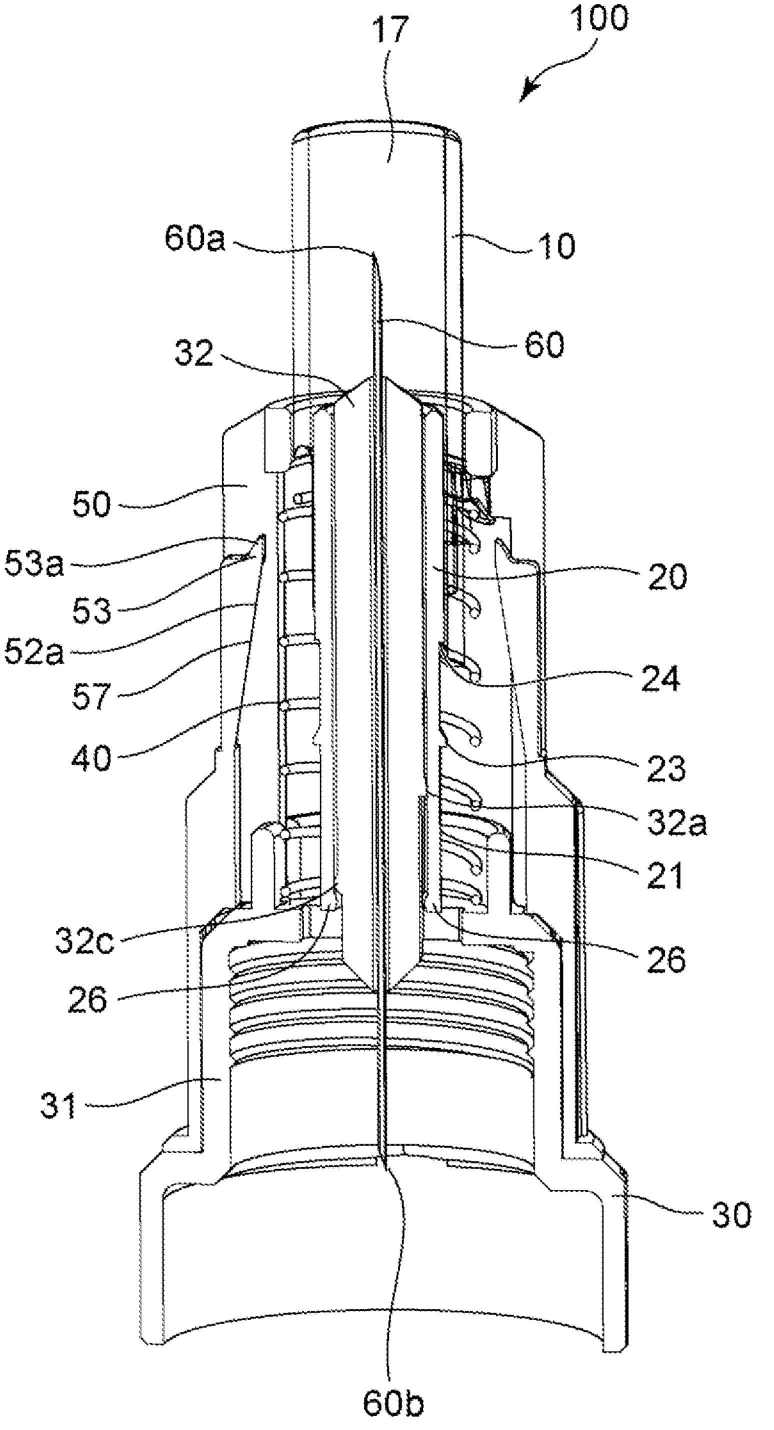
FIG. 2 is a cross-sectional view schematically showing the needle assembly according to the embodiment of the present disclosure.

A needle assembly 100 according to the embodiment of the present disclosure can be replaceably attached to a pen injector 200 including a medicinal solution therein. As shown in FIGS. 1A, 1B, and 2, the needle assembly 100 according to the embodiment of the present disclosure includes, as components, a casing 50 having an opening portion 51, and a movable needle cover portion 10, a tubular portion 20, a needle support portion 30 in which a hollow needle 60 is supported, and a biasing portion 40, each of which is configured to be at least partially accommodated in the casing 50. The needle assembly 100 according to the embodiment of the present disclosure further includes an overall cover 70 capable of covering these components before use. In use, this overall cover 70 can be removed (see FIG. 1A). The needle assembly 100 is configured by integrally combining the above components (the movable needle cover portion 10, the tubular portion 20, the needle support portion 30 with the hollow needle 60, the biasing portion 40, and the casing 50).

The components of the needle assembly 100 can be mainly made of a resin member except for the hollow needle 60. The constituent material of the resin member is not particularly limited, but may be at least one selected from the group consisting of polyethylene, polypropylene, polystyrene, and ABS (acrylonitrile butadiene styrene resin). The hollow needle 60 can be made of a metal member such as stainless steel.

Hereinafter, the term "in use of the needle assembly 100" as used herein refers to a state where at least the overall cover portion (not shown) is removed. The term "one direction" as used herein refers to a direction in which the movable needle cover portion 10 is pushed down and a medicinal solution injection-side end portion 60*a* of the hollow needle 60 can protrude outward. The term "opposite direction" as used herein refers to a direction opposite to a direction in which the medicinal solution injection-side end portion 60*a* of the hollow needle 60 protrudes outward, that is, a direction in which the movable needle cover portion 10 is pushed up and the medicinal solution injection-side end portion 60*a* is accommodated in the movable needle cover portion 10.

(Casing 50)

The casing 50 is configured to be capable of accommodating therein at least a part of each of the movable needle cover portion 10, the tubular portion 20, the needle support portion 30 with the hollow needle 60, and the biasing portion 40 (see FIGS. 1B, 2, and 7A to 7C). The casing 50 includes an opening portion 51 through which the movable needle cover portion 10 can pass and move. When the casing 50 has, for example, a substantially cylindrical shape, the opening portion 51 can be formed on an upper surface 56 side of the casing 50.

The casing 50 includes a locked portion 53 formed at a predetermined interval on a side surface 52 thereof and capable of being locked to a first needle cover portion projection portion 12 of the movable needle cover portion 10 described later. Specifically, at least a distal end side 53*a* of the locked portion 53 can be locked to the first needle cover portion projection portion 12 after completion of push-up movement in the opposite direction of the movable needle cover portion 10 described later. On the other hand, the locked portion 53 is not locked to the first needle cover portion projection portion 12 of the movable needle cover portion 10 before pushing-down movement (corresponding to before axial rotation) and in the middle stage of the pushing-down movement (corresponding to the middle stage of the axial rotation).

From the viewpoint of the positional relationship, after the completion of the push-up movement of the movable needle cover portion 10, the locked portion 53 of the casing 50 and the first needle cover portion projection portion 12 of the movable needle cover portion 10 have a positional relationship in which they face each other, a positional relationship in which they are coaxial, and/or a positional relationship in which they are on the same line. On the other hand, before the pushing-down movement and in the middle stage of the pushing-down movement of the movable needle cover portion 10, the locked portion 53 of the casing 50 and the first needle cover portion projection portion 12 of the movable needle cover portion 10 have a positional relationship in which they do not face each other, a positional relationship in which they are not coaxial, and/or a positional relationship in which they are not on the same line.

As an example, the casing 50 can have a second opening portion 55 on the side surface 52 as well as the opening portion 51 (hereinafter, referred to as a first opening portion) through which the movable needle cover portion 10 can pass. In this case, the locked portion 53 may correspond to the lower edge portion of the contour portion defining the second opening portion 55 formed in the side surface of the casing 50. In the embodiment of the present disclosure, a part of the first needle cover portion projection portion 12 described later protrudes outward through the second opening portion 55, and then a part of the protruding first needle cover portion projection portion 12 can be locked to the locked portion 53 (corresponding to the lower edge portion of the contour portion forming the second opening portion 55).

In order to suitably perform such locking, a slit 54 is preferably formed along the longitudinal direction of the side surface 52 from both ends of the locked portion 53 (corresponding to the lower edge portion of the contour portion forming the second opening portion 55). Since the slit 54 is formed, flexibility can be provided to the locked portion 53 (corresponding to the lower edge portion of the contour portion defining the second opening portion 55). As a result, it is possible to smoothly lock a part of the first needle cover portion projection portion 12 protruding outward through the second opening portion 55 to the locked portion 53 as compared with the case where the slit 54 is not formed.

Further, the locked portion 53 of the casing 50 preferably has the following form. Specifically, the inner side surface of the locked portion 53, which forms a part of an inner side surface 52*a* of the casing 50, is preferably a slope surface 57. The slope surface 57 (that is, the inclined surface) is a surface continuing downward and inward from the distal end side 53*a* of the locked portion 53. Specifically, the slope surface 57 is configured to be gradually inclined inward toward the distal end side 53*a*.

With this configuration, the thickness of the locked portion 53 can be increased toward the distal end side 53*a*. Therefore, since the strength of the locked portion 53 is improved as a whole, the locked state can be continuously maintained even after the first needle cover portion projection portion 12 is locked to the distal end side 53*a* of the locked portion 53.

On the other hand, with such a configuration, in the locked portion 53, the thickness of the locked portion 53 can be reduced toward the side opposite to the distal end side 53*a*. Therefore, since the flexibility of the locked portion 53 is improved as a whole, the first needle cover portion projection portion 12 can be easily locked to the distal end side 53*a* of the locked portion 53.

The number of slope surfaces 57 corresponds to the number of first needle cover portion projection portions 12 of the movable needle cover portion 10. In one example, when the number of first needle cover portion projection portions 12 is two, the number of slope surfaces 57 is also two correspondingly. In particular, when two first needle cover portion projection portions 12 are arranged to face each other, two slope surfaces 57 are also arranged to face each other correspondingly (see FIGS. 7B and 7C).

When the inner side surface of the locked portion is a straight portion extending in the vertical direction and the distal end side of the locked portion is in the form of a latch (claw) portion partially extending inward from the same straight surface, a steep wall-shaped inner side surface can be formed between the same straight portion and the latch (claw) portion. Therefore, the first needle cover portion projection portion 12 may be caught on the steep wall-shaped inner side surface.

On the other hand, when the slope surface 57 gradually inclined is formed on the inner side surface of the locked portion 53, it is possible to suitably avoid the first needle cover portion projection portion 12 from being caught on the inner side surface of the locked portion 53 until the first needle cover portion projection portion 12 is locked to the distal end side 53*a* of the locked portion 53 in the middle of the push-up movement of the movable needle cover portion 10 described later.

More preferably, the slope surface 57 on which the first needle cover portion projection portion 12 can come into contact with the locked portion 53 can be formed only in a central region 53*b* rather than the entire inner side surface of the locked portion 53. As a result, the contact area between the first needle cover portion projection portion 12 and the inner side surface of the locked portion 53 can be reduced in the middle of the push-up movement of the movable needle cover portion 10 described later. Therefore, since the contact resistance between the two can be reduced, the push-up movement of the movable needle cover portion 10 can be more smoothly performed.

Note that rib portions 58 arranged at a predetermined interval can be further provided in a lower region of an outer side surface 52*b* of the casing 50. The presence of such rib portions 58 allows the rib portions 58 to function as a finger grip portion upon removal of the pen injector 200 from the needle assembly 100 after use of the needle assembly 100. Specifically, the pen injector 200 can be removed from the needle support portion 30, that is, from the needle assembly

100 by hooking a finger on the rib portions 58 (or rib portions 31*c* provided on the outer surface of a base portion 31 of the needle support portion 30) and axially rotating the pen injector 200.

(Movable Needle Cover Portion 10)

The movable needle cover portion 10 covers the hollow needle 60 which is supported by the needle support portion 30 when not in use and through which the medicinal solution can flow, and is movable through the opening portion 51 of the casing 50 in one direction such that the injection-side end portion 60*a* for the medicinal solution of the hollow needle 60 protrudes outward when in use (see FIGS. 1A to 3).

Specifically, when not in use, a part of the movable needle cover portion 10 covers the hollow needle 60 located outside the opening portion 51 of the casing 50, and the remaining part is accommodated in the casing 50. On the other hand, in use, by pushing down the movable needle cover portion 10 in the opening portion 51 of the casing 50, the injection-side end portion 60*a* for the medicinal solution of the hollow needle 60 can protrude outward. At this time, substantially the entire movable needle cover portion 10 can be accommodated in the casing 50.

The movable needle cover portion 10 has a substantially cylindrical shape, and the tubular portion 20 is positioned in an inner region 17 thereof. The movable needle cover portion 10 includes one or more first needle cover portion projection portions 12 formed on the outer side surface 11. In one example, two first needle cover portion projection portions 12 arranged to face each other are provided.

The shape of the first needle cover portion projection portion 12 is a shape that can be locked to the locked portion 53 of the casing 50 when the movable needle cover portion 10 moves in the pushing-down direction (one direction). In addition, the shape of the first needle cover portion projection portion 12 is a shape that is not locked to the locked portion 53 of the casing 50 and can pass over the locked portion 53 when the movable needle cover portion 10 moves in the pushing-up direction (opposite direction).

As an example, the first needle cover portion projection portion 12 has a wing shape. Specifically, the first needle cover portion projection portion 12 can be a wing-shaped member having one end 12*a* attached to the outer side surface 11 of the movable needle cover portion 10 and the other end 12*b* directed downward toward a side surface lower end portion 16. Preferably, the first needle cover portion projection portion 12 can include a configuration in which a distance between the outer side surface 11 and the first needle cover portion projection portion 12 (wing portion) gradually increases toward the other end 12*b* from a viewpoint of increasing a locking space with the locked portion 53 of the casing 50 as much as possible.

The movable needle cover portion 10 having a substantially cylindrical shape can have an inclined surface 13 at the side surface lower end portion 16 thereof. As will be described later, it is not essential that the movable needle cover portion 10 has the inclined surface 13 at the side surface lower end portion 16, and it is sufficient that at least one of the side surface lower end portion 16 and a first tubular portion projection portion 22 of the tubular portion 20 has the inclined surface.

The movable needle cover portion 10 having a substantially cylindrical shape includes a notch portion 15 continuous with the side surface lower end portion 16 capable of abutting on the first tubular portion projection portion 22 described later. The notch portion 15 can be formed by forming a part 14 of the side surface lower end portion 16 in a concave shape in the pushing-up direction (corresponding to the opposite direction) of the movable needle cover portion 10. That is, the side surface lower end portion 16 of the movable needle cover portion 10 includes a portion abutting on the first tubular portion projection portion 22 and a convex portion continuous with the abutting portion.

The position of the notch portion 15 is adjusted such that the notch portion 15 and the first tubular portion projection portion 22 described later can be substantially coaxial after the axial rotation of the movable needle cover portion 10. As a result, the movable needle cover portion 10 after completion of the axial rotation can be further pushed down and moved in one direction (pushing-down direction) without abutting on the first tubular portion projection portion 22 again.

The movable needle cover portion 10 further includes a second needle cover portion projection portion 19 on the inner side surface 18. The second needle cover portion projection portion 19 can be formed, for example, inside the side surface lower end portion 16 of the movable needle cover portion 10. The second needle cover portion projection portion 19 has the following features. Specifically, when moving the movable needle cover portion 10 in the pushing-down direction, the second needle cover portion projection portion 19 can get over the second tubular portion projection portion 23 of the tubular portion 20 described later, but once getting over the second tubular portion projection portion 23, the second needle cover portion projection portion 19 cannot get over the second tubular portion projection portion 23 again along the pushing-up direction of the movable needle cover portion 10 and is locked to the second tubular portion projection portion 23.

Furthermore, the movable needle cover portion 10 further includes a third needle cover portion projection portion 11*a* partially formed at a predetermined interval on the outer side surface 11. Specifically, the third needle cover portion projection portion 11*a* can be arranged between the first needle cover portion projection portion 12 and the side surface lower end portion 16 and inside the biasing portion 40 provided to surround the outer side surface 11 of the movable needle cover portion 10 described later. With such an arrangement mode, a minute clearance can be provided between the biasing portion 40 and the outer side surface 11 of the movable needle cover portion 10 (the main portion not provided with the third needle cover portion projection portion 11*a*).

As described later, the movable needle cover portion 10 is movable in one direction (pushing-down direction) and a direction opposite to the one direction (pushing-up direction). Specifically, along with the movement of the movable needle cover portion 10 in one direction (pushing-down direction), the compression coil spring as the biasing portion 40 temporarily contracts, and a force to expand acts on the compression coil spring that has contracted once, so that the movable needle cover portion 10 can be moved in the opposite direction (pushing-up direction). That is, the biasing portion 40 contracts or expands along with the movement of the movable needle cover portion 10. In this regard, the contact area between the movable needle cover portion 10 and the biasing portion 40 can be reduced as much as possible by providing the minute clearance. As a result, it is possible to smoothly perform both the axial movement of the movable needle cover portion 10 and the contraction and expansion behavior of the biasing portion 40.

(Tubular Portion 20)

The tubular portion 20 is arranged on the needle support portion 30, specifically, on the base portion 31 of the needle support portion 30, and is configured such that the movable needle cover portion 10 and a part thereof can abut on each other. The tubular portion 20 has a substantially cylindrical shape and can be positioned in the inner region 17 of the movable needle cover portion 10. In the inner region 25 of the tubular portion 20 having a substantially cylindrical shape, the extending portion 32 of the needle support portion 30 with the hollow needle 60 is movable along the longitudinal direction (see FIGS. 1B, 2, 4A and 4B).

The first tubular portion projection portion 22 is provided on an outer side surface 21 of the tubular portion 20. Specifically, the first tubular portion projection portion 22 is provided on the outer side surface 21 of the tubular portion 20 so as to extend in a direction substantially perpendicular to the longitudinal direction (or the extending direction or the axial direction) of the tubular portion 20. The position of the first tubular portion projection portion 22 is adjusted so as to be able to abut on the side surface lower end portion 16 of the movable needle cover portion 10 that moves in the pushing-down direction in use. The first tubular portion projection portion 22 extending in a direction substantially perpendicular to the longitudinal direction of the tubular portion 20 has a substantially circular shape in a cross-sectional view or a side view.

The first tubular portion projection portion 22 does not necessarily have a substantially circular shape in a cross-sectional view or a side view, and may have an inclined surface. That is, it is sufficient that at least one of the side surface lower end portion 16 of the movable needle cover portion 10 and the first tubular portion projection portion 22 of the tubular portion 20 has the inclined surface. With such a configuration, when the movable needle cover portion 10 is moved in the pushing-down direction in use and the side surface lower end portion 16 abuts on the first tubular portion projection portion 22 of the tubular portion 20, an axial rotational force can be applied to the movable needle cover portion 10 that is pushed down.

Note that, in order to suitably apply the axial rotational force to the movable needle cover portion 10, it is preferable that the tubular portion 20, which is a counterpart abutted at the time of axial rotation of the movable needle cover portion 10, is supported on the upper surface of the base portion 31 of the needle support portion 30 without axial rotation. As a result, the movable needle cover portion 10 to be pushed down can be suitably axially rotated.

The outer side surface 21 of the tubular portion 20 includes a first outer side surface 21*a* having a relatively large thickness and a second outer side surface 21*b* having a relatively smaller thickness than the first outer side surface 21*a*. Specifically, on the outer side surface 21 of the tubular portion 20, the first outer side surface 21*a* having a relatively large thickness and the second outer side surface 21*b* having a relatively small thickness are alternately arranged.

With such a configuration, the tubular portion 20 can further include the second tubular portion projection portion 23 and a step portion 24 at a predetermined interval on the outer side surface 21 thereof. As for the positional relationship between the second tubular portion projection portion 23 and the step portion 24, the former is positioned on the pushing-down direction side (that is, the lower side) with the second outer side surface 21*b* interposed therebetween, and the latter is positioned on the pushing-up direction side (that is, the upper side) with the second outer side surface 21*b* interposed therebetween.

The second tubular portion projection portion 23 is configured such that the second needle cover portion projection portion 19 can get over the second tubular portion projection portion 23 when the movable needle cover portion 10 is moved in the pushing-down direction, and is configured such that the second needle cover portion projection portion 19 cannot get over the second tubular portion projection portion 23 again along the pushing-up direction of the movable needle cover portion 10 once the second needle cover portion projection portion 19 gets over the second tubular portion projection portion 23 and is locked to the second tubular portion projection portion 23. By such locking, as will be described in a preferred mode described later, the tubular portion 20 can move integrally with the movable needle cover portion 10 after the axial rotation, and the tubular portion 20 can partially protrude and move from the opening portion of the movable needle cover portion 10. As a result, in a case where the tubular portion 20 is a colored member, it is possible to determine whether the hollow needle 60 is used visually from the outside.

Even if a force in the pushing-up direction acts on the movable needle cover portion 10 before the movable needle cover portion 10 is moved in the pushing-down direction, the step portion 24 can be locked to the second needle cover portion projection portion 19 located inside the movable needle cover portion 10. Furthermore, the first needle cover portion projection portion 12 can be locked to the upper surface 56 or the side surface 52 forming the opening portion 51 of the casing 50.

By the locking of both, it is possible to suitably avoid detachment of the movable needle cover portion 10 from the casing 50 when the needle assembly 100 is not used. Therefore, it is possible to suitably avoid the hollow needle 60 from being exposed to the outside when the needle assembly 100 is not used. Thus, the safety of the needle assembly 100 when not in use can also be suitably ensured.

The tubular portion 20 further includes third tubular portion projection portions 26 at the lower end of the inner region 25 of the tubular portion 20 having a substantially cylindrical shape. The third tubular portion protrusion portion 26 is configured to be engageable with a first needle support portion protrusion portion 32*a* formed on an outer surface of the extending portion 32 of the needle support portion 30 described later. Specifically, the third tubular portion protrusion portion 26 is configured to be located coaxially with the first needle support portion protrusion portion 32*a* and below the first needle support portion protrusion portion 32*a*. More specifically, the third tubular portion protrusion portion 26 is arranged at a position where the tubular portion 20 that has partially protruded and moved from the opening portion of the movable needle cover portion 10 cannot further move to the outside.

As a result, even if a pulling force acts on the movable needle cover portion 10 to the outside, the tubular portion 20 can be suitably avoided from being detached accordingly. Furthermore, regardless of the magnitude of the amount of movement of the movable needle cover portion 10 in the pushing-down direction, the region in which the tubular portion 20 partially protrudes from the opening portion of the movable needle cover portion 10 can be made constant.

The tubular portion 20 further includes a slit 27 on the lower end side thereof. As a result, flexibility can be provided to the lower end side of the tubular portion 20. As a result, the first needle support portion protrusion portion 32*a* of the needle support portion 30 described later can be easily passed through the slit 27 having flexibility.

(Biasing Portion 40)

The biasing portion 40 is configured such that the movable needle cover portion 10 is biased in the opposite direction (pushing-down direction) along with the movement of the movable needle cover portion 10 in one direction (pushing-up direction). Specifically, the biasing portion 40 is provided so as to surround the outer side surface 11 of the movable needle cover portion 10. In addition, the biasing portion 40 is arranged between an upper surface 31*a* of the base portion 31 of the needle support portion 30 and the first needle cover portion projection portion 12 such that one end thereof is in contact with the upper surface 31*a* of the base portion 31 of the needle support portion 30 and the other end thereof is in contact with the first needle cover portion projection portion 12 of the movable needle cover portion 10.

Although not particularly limited, a compression coil spring can be used as the biasing portion 40. In the case of using the compression coil spring, the compression coil spring located between the base portion 31 of the needle support portion 30 and the first needle cover portion projection portion 12 temporarily contracts along with the movement of the movable needle cover portion 10 in one direction (pushing-down direction). The movable needle cover portion 10 can be moved in the opposite direction (pushing-up direction) by the action of the force to expand on the compression coil spring that has contracted once.

(Needle Support Portion 30)

The needle support portion 30 supports the hollow needle 60 through which the medicinal solution can flow (see FIGS. 1B, 2, 5A, and 5B). The needle support portion 30 has the base portion 31 and the extending portion 32 integrally configured with the base portion 31. The base portion 31 of the needle support portion 30 has a space region therein, and can accommodate a non-injection-side end portion 60*b* on the opposite side to the medicinal solution injection-side end portion 60*a* of the needle 60. Also, the base portion 31 may have the rib portions 31*c* on its outer surface which serve as a finger grip portion when the pen injector 200 is removed from the needle assembly 100 after use of the needle assembly 100.

The inner surface of the base portion 31 of the needle support portion 30 can be connected to and held by the outer surface of the pen injector 200. As a method of connecting and holding the two, a thread joining method using a combination of a male thread and a female thread, or the like can be used. The base portion 31 can have any form provided that the inner surface of the base portion 31 and the outer surface of the pen injector 200 can be connected and held with each other. As an example, FIG. 1B and the like show an aspect in which the base portion 31 has a flange portion on the lower end side thereof, but the base portion 31 does not necessarily need to have the flange portion on the lower end side thereof, and the inner space of the portion of the inner space of the base portion 31 into which the pen injector 200 is inserted may have substantially the same diameter as a whole. In the aspect shown in FIG. 1B and the like, the rib portions 31*c* are formed in the flange portion of the base portion 31, but the present invention is not limited thereto, and the rib portion may be formed at a predetermined position of the outer surface of the base portion corresponding to a position where the inner surface of the base portion 31 and the outer surface of the pen injector 200 are connected and held.

With such a configuration, it is possible to avoid the non-injection-side end portion 60*b* of the needle 60 from being exposed to the outside from the base portion 31 of the needle support portion 30, thereby avoiding the user of the needle assembly 100 from being accidentally pierced with the non-injection-side end portion 60*b*.

The extending portion 32 of the needle support portion 30 is positioned to protrude from the upper surface of the base portion 31. The extending portion 32 is slidable in the inner region 25 of the tubular portion 20 having a substantially cylindrical shape along the longitudinal direction. In order to enable such sliding movement, the width dimension of the extending portion 32 is preferably substantially the same as the width dimension of the inner region 25 of the tubular portion 20 having a substantially cylindrical shape. As a result, when the movable needle cover portion 10 is moved in the pushing-down direction to cause the medicinal solution injection-side end portion 60*a* of the needle to protrude outward, the protruding direction of the needle can be fixed.

The extending portion 32 includes the first needle support portion protrusion portion 32*a* on the outer surface. The first needle support portion protrusion portion 32*a* is configured to be locked to the third tubular portion projection portion 26 of the tubular portion 20 and to be located coaxially with the projection portion 26 and above the third tubular portion projection portion 26. With such a configuration, it is possible to avoid detachment of the tubular portion 20 and to make the region of the tubular portion 20 partially protruding from the opening portion of the movable needle cover portion 10 constant.

Figure 5A:
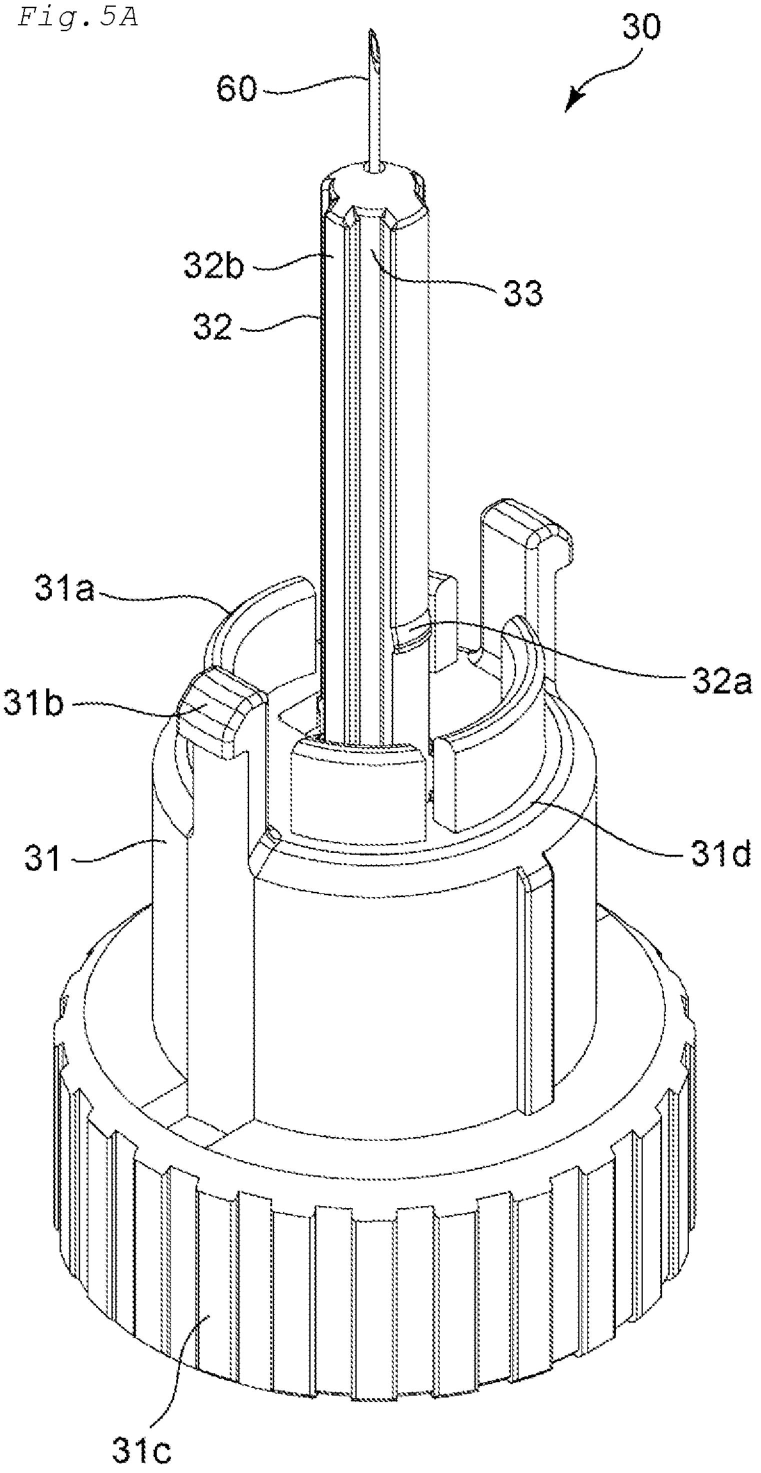
FIG. 5A is a perspective view schematically showing a needle support portion (with a hollow needle).
Figure 5B:
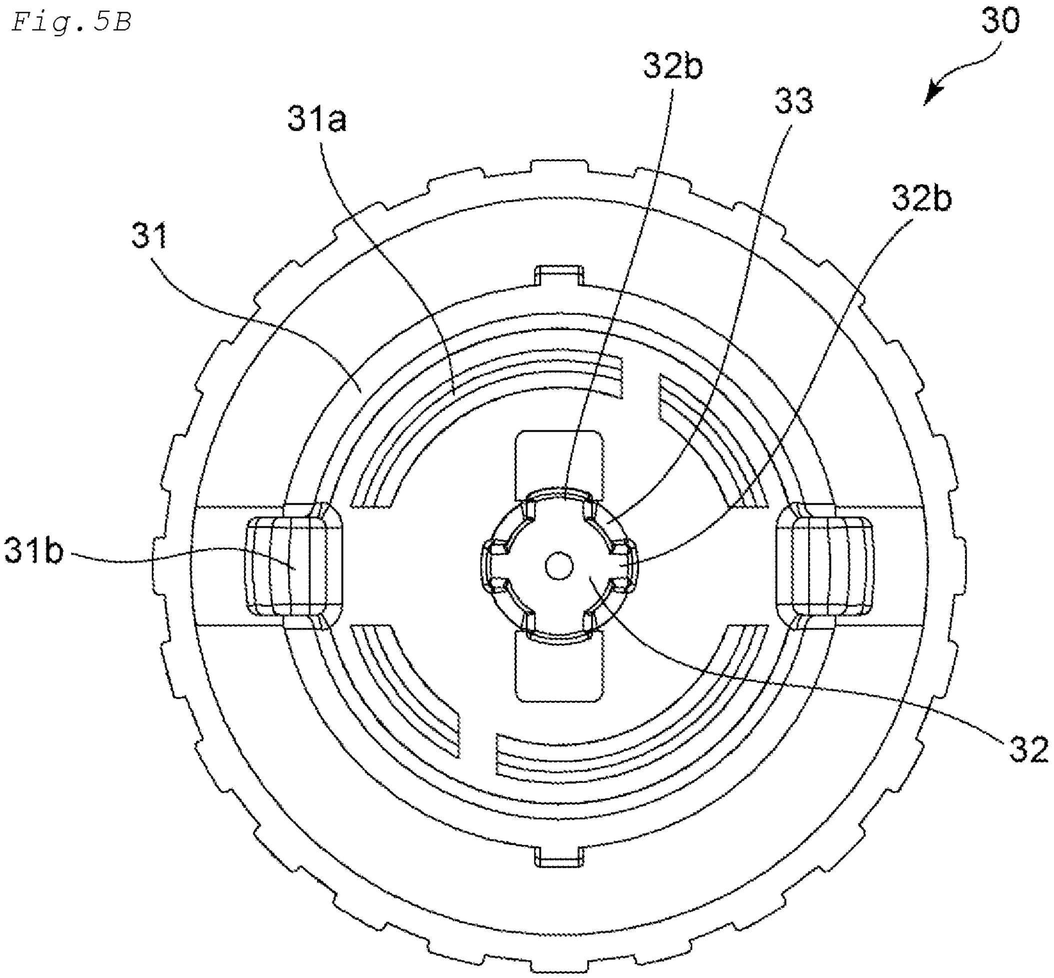
FIG. 5B is a plan view schematically showing the needle support portion.
Figure 6:
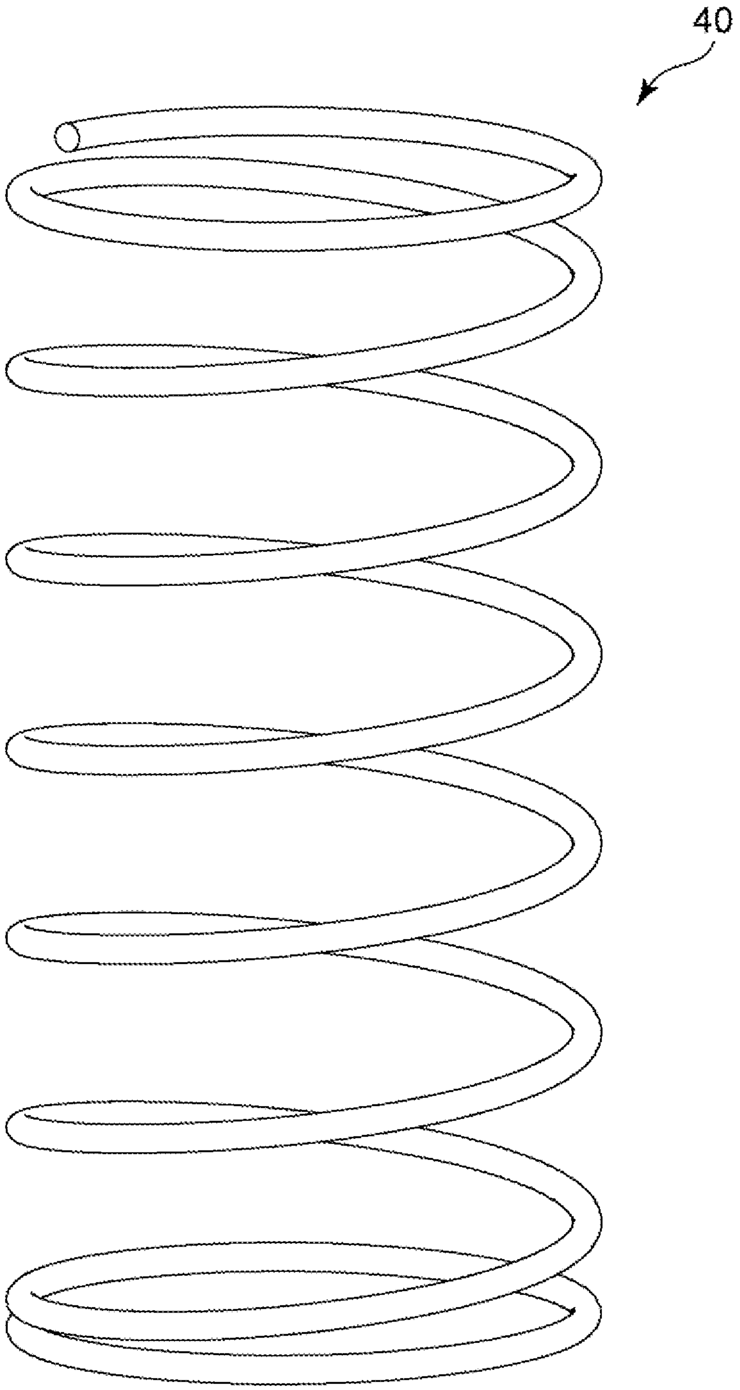
FIG. 6 is a cross-sectional view schematically showing a biasing portion.
Figure 7A:
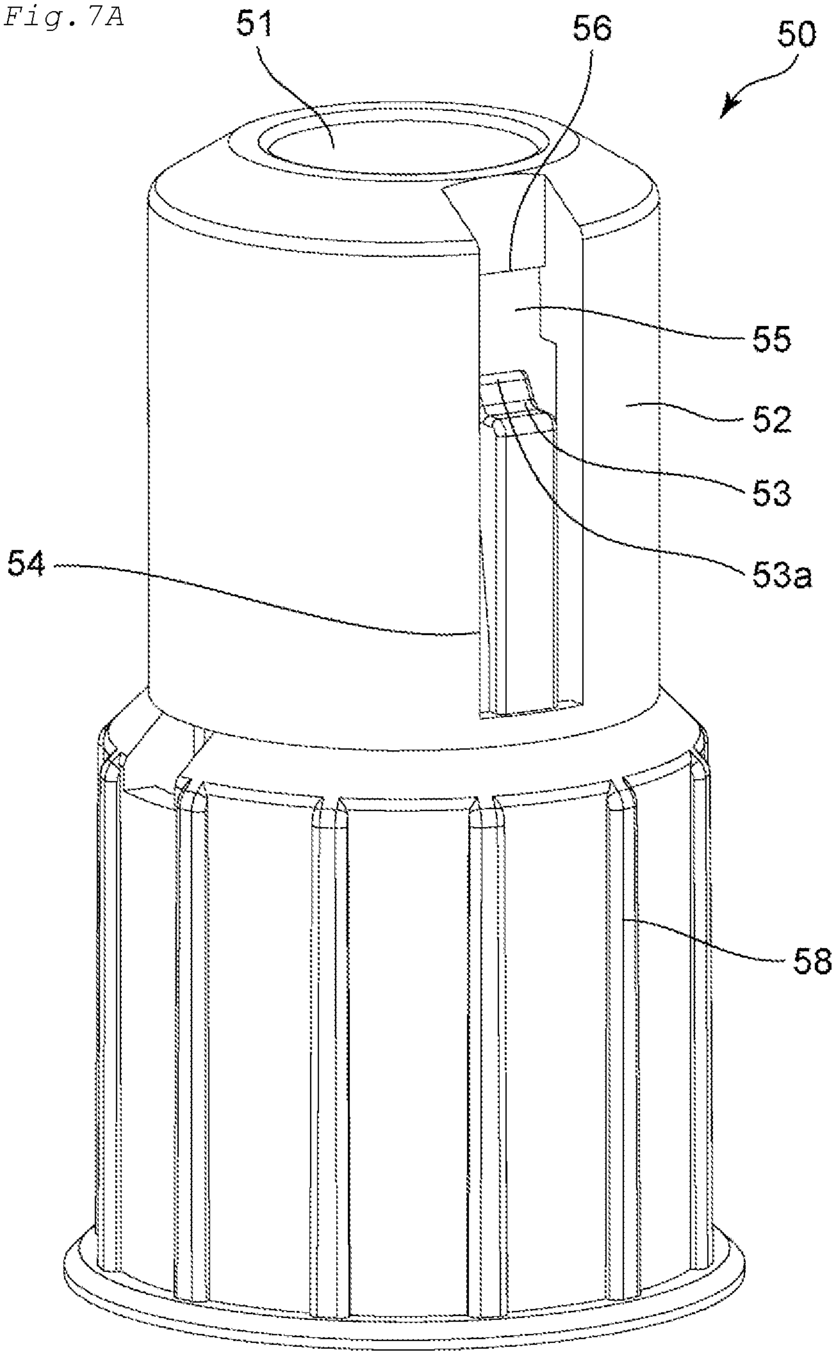
FIG. 7A is a perspective view schematically showing a casing.
Figure 7B:
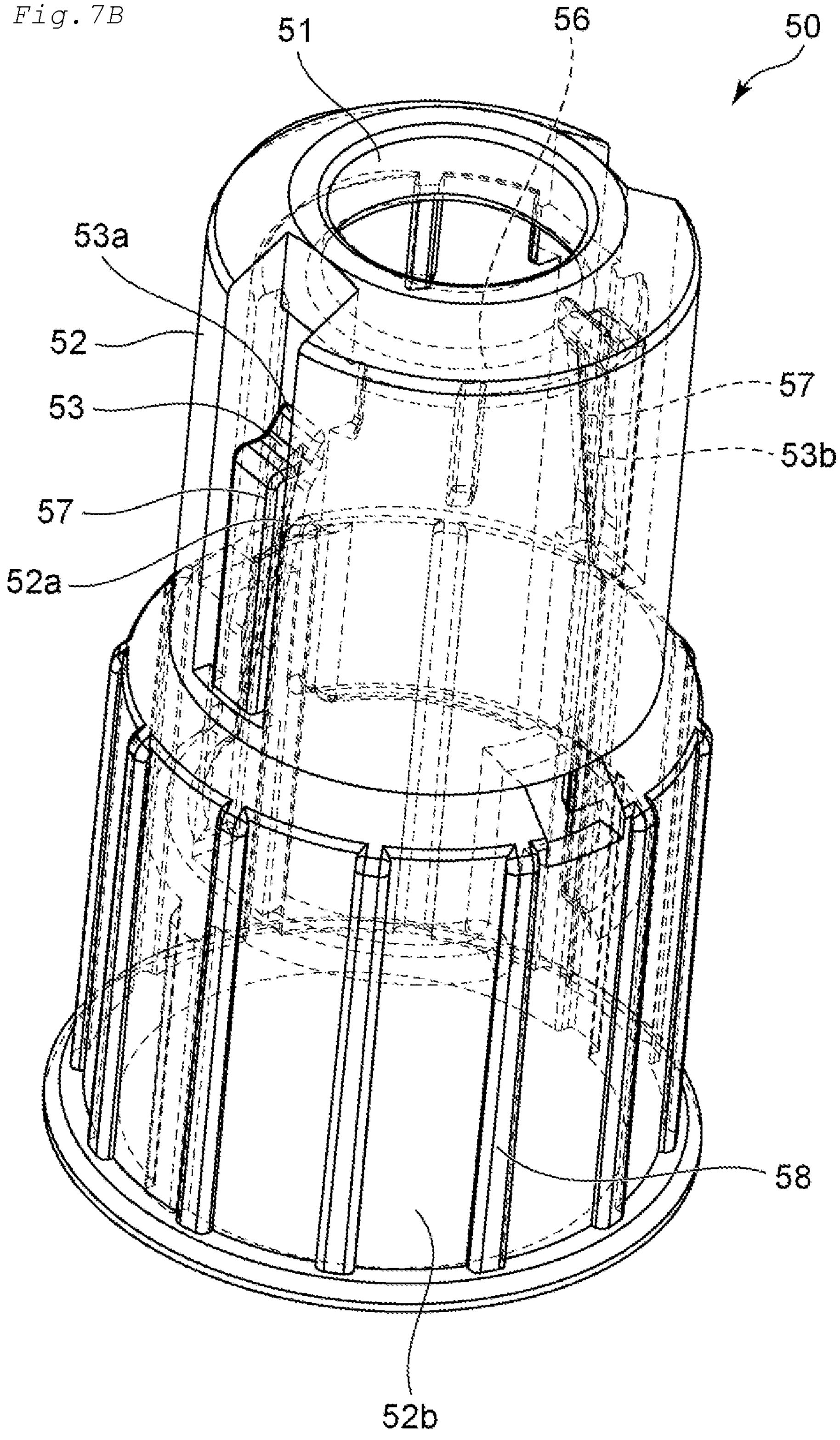
FIG. 7B is a perspective view schematically showing the casing in which an internal structure is visually recognizable.
Figure 7C:
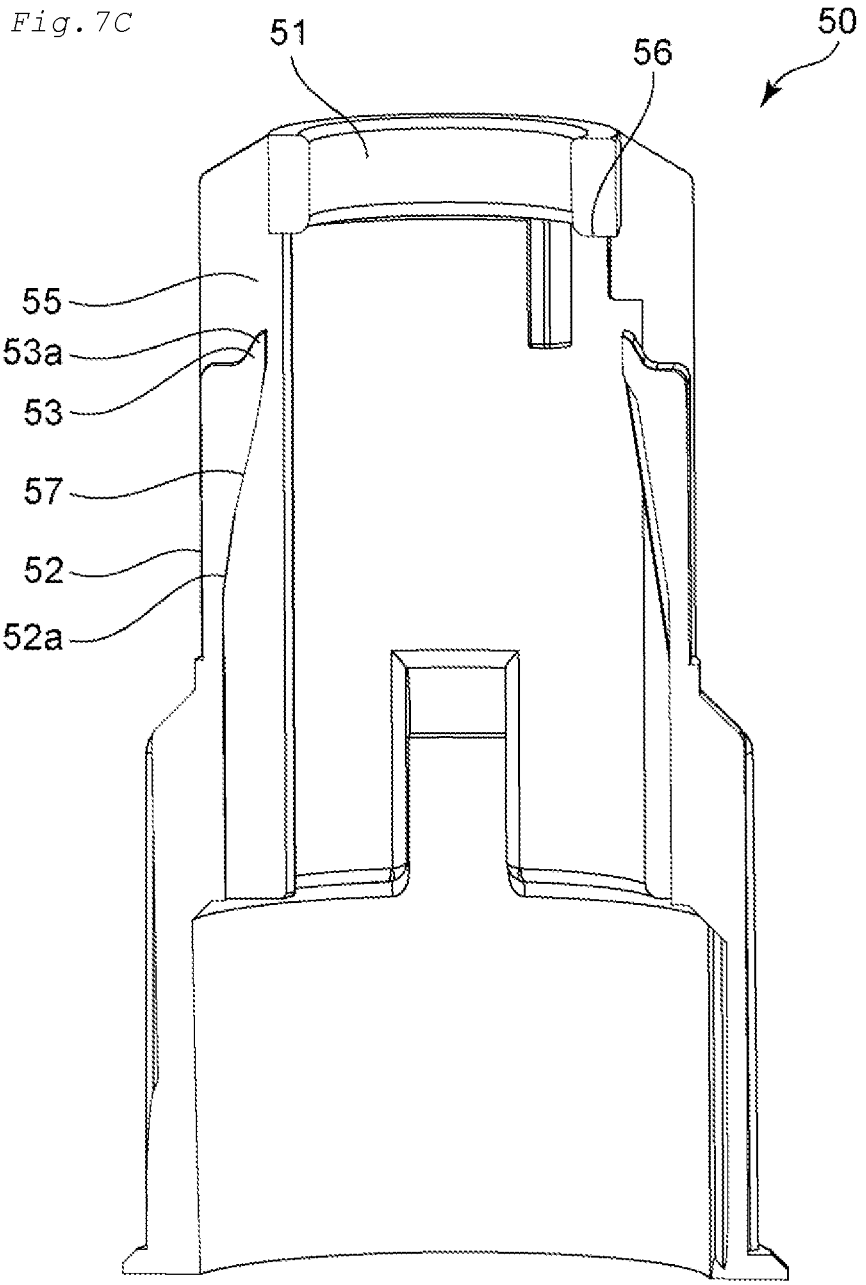
FIG. 7C is a cross-sectional view schematically showing the casing.

In addition, the extending portion 32 includes convex portions 32*b* arranged at predetermined intervals along the periphery thereof in a plan view at the base portion side end portion (see FIG. 5B). With such a configuration, the concave portions 33 can be formed at predetermined intervals. The concave portions 33 and the third tubular portion protrusion portions 26 of the tubular portion 20 can be fitted to each other. As a result, it is possible to suitably avoid the tubular portion 20 from axially rotating with respect to the extending portion 32 of the needle support portion 30. Since the slit 27 is formed on the lower end side of the tubular portion 20 as described above, flexibility can be provided to the lower end side of the tubular portion 20. As a result, the first needle support portion protrusion portion 32*a* of the needle support portion 30 can be easily passed through the slit 27 having flexibility. As a result, it is possible to smoothly install the tubular portion 20 on the extending portion 32 of the needle support portion 30.

The extending portion 32 can further include a second needle support portion protrusion portion 32*c* at the base portion side end portion of the formation region of the concave portion 33. Before the start of use of the needle assembly 100, the second needle support portion protrusion portion 32*c* is located above the third tubular portion projection portion 26 located at the lower end of the inner region 25 of the tubular portion 20 and is arranged so as to be slightly in contact with the third tubular portion projection portion 26. With such a configuration, it is possible to avoid easy removal of the tubular portion 20 before the start of use of the needle assembly 100.

Further, the base portion 31 can further include a bank portion 31*a* extending coaxially with the extending portion 32 from the contour portion of the upper surface 31*a* thereof. As described above, one end of the biasing portion 40 is arranged so as to be in contact with the upper surface 31*a* of the base portion 31 of the needle support portion 30. In this case, the biasing portion 40 is preferably arranged inside the bank portion 31*a*. With such an arrangement, the bank portion 31*a* can function as a stopper for positional displacement of the biasing portion 40 in a direction substantially perpendicular to the contraction/expansion direction (that is, in the lateral direction,). Therefore, the positional displacement of the biasing portion 40 can be suitably suppressed.

(Overall Cover Portion 70)

Figure 8:
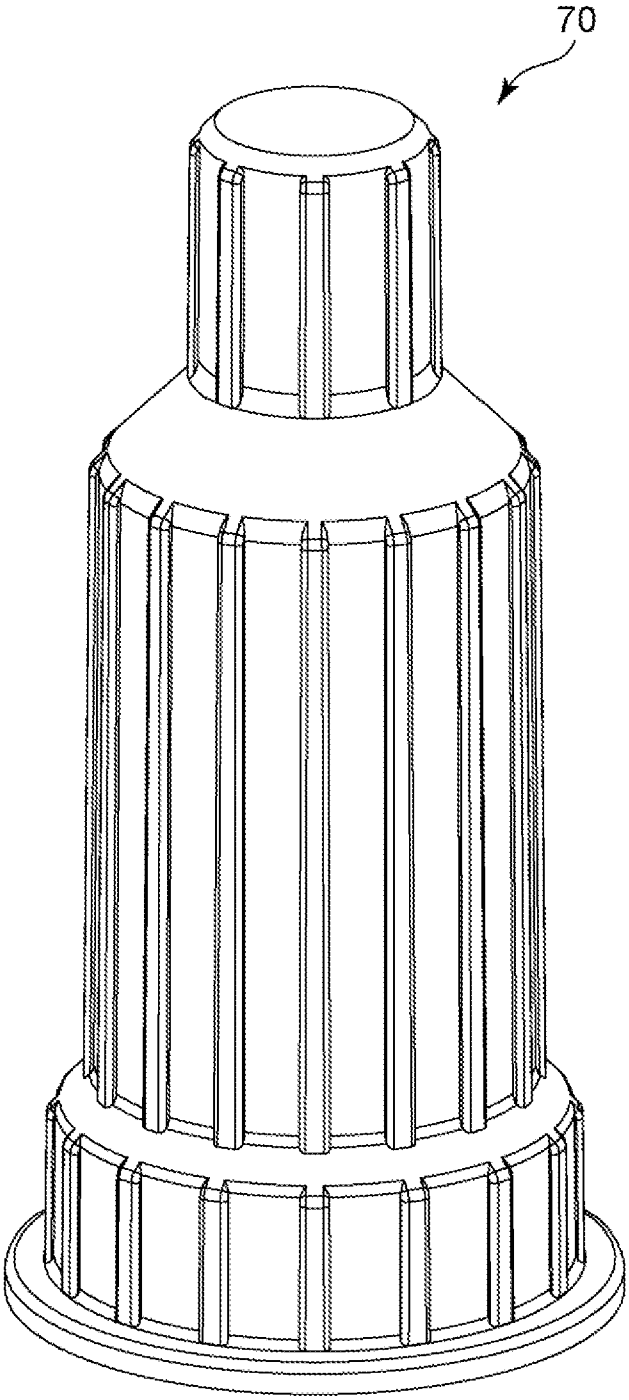
FIG. 8 is a perspective view schematically showing the overall cover.

The overall cover portion 70 only needs to be able to accommodate the integrally combined components (the movable needle cover portion 10, the tubular portion 20, the needle support portion 30 with the hollow needle 60, the biasing portion 40, and the casing 50) of the needle assembly 100 before attachment of these components to the pen injector 200 (see FIG. 8). From the viewpoint of safety and hygiene, it is preferable that the overall cover portion 70 has an opening portion for accommodating the integrally combined components therein sealed before use of the needle assembly 100.

(Features of Present Disclosure)

The embodiment of the present disclosure has the following technical features in a state where at least the movable needle cover portion 10, the tubular portion 20, the needle support portion 30, the biasing portion 40, and the casing 50 are integrally combined (see FIGS. 1B and 2).

Specifically, in the embodiment of the present disclosure, by the movement of the movable needle cover portion 10 in one direction, at least the movable needle cover portion 10 abuts on the tubular portion 20 to be axially rotated from a predetermined position before the movement to another position, whereby the movable needle cover portion 10 "after the axial rotation" can be moved in a direction opposite to the one direction by the biasing portion 40. Furthermore, in the embodiment of the present disclosure, the movable needle cover portion 10 "after the axial rotation, which has completed the movement in the opposite direction, is completed" can be locked to the casing 50. The term ""at least" the movable needle cover portion 10 is axially rotated" as used herein refers to that at least the movable needle cover portion is included as an object to be axially rotated, that is, one or more objects to be axially rotated are included.

According to the above feature, when the needle assembly 100 is in use, the movable needle cover portion 10 can be biased by the biasing portion 40 along with the movement of the movable needle cover portion 10 in one direction (pushing-down direction). Therefore, the movable needle cover portion 10 moved in the one direction can move in a direction (pushing-up direction) opposite to the one direction. As a result, the medicinal solution injection-side end portion 60*a* of the needle 60 that has once protruded outward from the movable needle cover portion 10 can be "automatically" accommodated inside the needle cover portion 10.

In addition, according to the above feature, since the movable needle cover portion 10 "after the axial rotation, which has completed the movement in the opposite direction (pushing-up direction)" and the casing 50 can be locked, it is possible to suppress the movable needle cover portion 10, which has completed the movement in the opposite direction, from re-moving in one direction (pushing-down direction) by such locking. As a result, it is possible to avoid re-protrusion of the used hollow needle 60 from the movable needle cover portion 10.

In addition, in the embodiment of the present disclosure, only by using the biasing portion 40, the axial rotation of the movable needle cover portion 10, and the locking between the movable needle cover portion 10 and the casing 50, automatic accommodation of the medicinal solution injection-side end portion 60*a* of the needle 60 and avoidance of re-protrusion of the used needle 60 are achieved. That is, by using the needle assembly 100 having a simple structure as a whole, it is possible to automatically accommodate the medicinal solution injection-side end portion 60*a* of the needle 60 and to avoid re-protrusion of the used needle 60. Also in this respect, the embodiment of the present disclosure has technical features.

Note that the needle assembly 100 according to the embodiment of the present disclosure preferably adopts the following aspects.

In one aspect, the tubular portion 20 is preferably movable integrally with the movable needle cover portion 10 after the axial rotation.

As described above, in the embodiment of the present disclosure, the movable needle cover portion 10 after the axial rotation is movable in the opposite direction (pushing-up direction). At this time, since the tubular portion 20 is integrally movable together with the movable needle cover portion 10 after the axial rotation, the tubular portion 20 is also movable in the opposite direction (pushing-up direction) in addition to the movable needle cover portion 10 after the axial rotation. In addition, as described above, in the embodiment of the present disclosure, in the movable needle cover portion 10 after the axial rotation, which has completed the movement in the opposite direction (pushing-up direction), is completed", the movable needle cover portion 10, which has completed the movement in the opposite direction, is suppressed from re-moving in one direction (pushing-down direction). Therefore, the tubular portion 20 that moves integrally with the movable needle cover portion 10 can also be suppressed from re-moving in one direction (pushing-down direction).

At this time, when the movement of the movable needle cover portion 10 in the opposite direction (pushing-up direction) is completed, it is particularly preferable that a part of the tubular portion 20 integrally movable with the movable needle cover portion 10 can protrude from at least the opening portion 51 of the casing 50.

First, as described above, since the tubular portion 20 that has integrally moved in the opposite direction (pushing-up direction) together with the movable needle cover portion 10 is suppressed from re-moving in one direction (pushing-down direction), when the tubular portion 20 is configured to be able to protrude from the opening portion 51 of the casing 50 at the completion of the movement of the movable needle cover portion 10 in the pushing-up direction, the protruding state can be fixed and maintained. Secondly, when the movement of the movable needle cover portion 10 in the opposite direction (pushing-up direction) is completed, the injection of the medicinal solution into the body using the hollow needle 60 is already completed. That is, when the movement of the movable needle cover portion 10 in the opposite direction (pushing-up direction) is completed, the hollow needle 60 is in a used state.

In view of the above, the tubular portion 20 in which the protruding state from the opening portion 51 of the casing 50 is fixedly maintained can be used as a determination element for determining whether the hollow needle 60 is used. In particular, when the movable needle cover portion 10 is transparent or translucent, and the tubular portion 20 is the colored marker portion, the colored tubular portion 20 maintained protruding from the opening portion 51 of the casing 50 can be visually recognized from the outside through the movable needle cover portion 10. Therefore, it is possible to easily determine that the hollow needle 60 has been used.

As a result, it is possible to suitably avoid a medical worker or the like from erroneously using the used needle assembly. In addition, even when the used needle assembly is erroneously mixed in the sample group of the needle assembly before the completion of the medicinal solution administration, a medical worker or the like can determine that the needle assembly in which the tubular portion 20 functioning as the marker portion can be visually recognized from the outside is a used needle assembly and can suitably remove the needle assembly from the sample group of the needle assembly before the completion of the medicinal solution administration.

From the above, according to the present aspect, the tubular portion 20 not only functions to axially rotate the movable needle cover portion 10 but also functions as a colored marker portion for determining whether the hollow needle 60 has been used. That is, according to the present aspect, in determining whether the hollow needle 60 has been used, it is not necessary to separately prepare, for example, a ring-shaped colored marker portion, and thus, it is possible to suitably avoid an excessive increase in the number of components of the needle assembly 100.

Hereinafter, an operation mode of the needle assembly 100 according to the embodiment of the present disclosure will be described.

As described above, in the embodiment of the present disclosure, at least the movable needle cover portion 10 abuts on the tubular portion 20 and is axially rotatable by the movement of the movable needle cover portion 10 in one direction. As an example, the axial rotation target can be the movable needle cover portion 10 alone. Hereinafter, a case where the axial rotation target is the movable needle cover portion 10 alone will be described as an example. However, such an aspect is merely an example, and an aspect in which the tubular portion 20 can also be an axial rotation target in addition to the movable needle cover portion 10 can also be adopted.

Figure 9A:
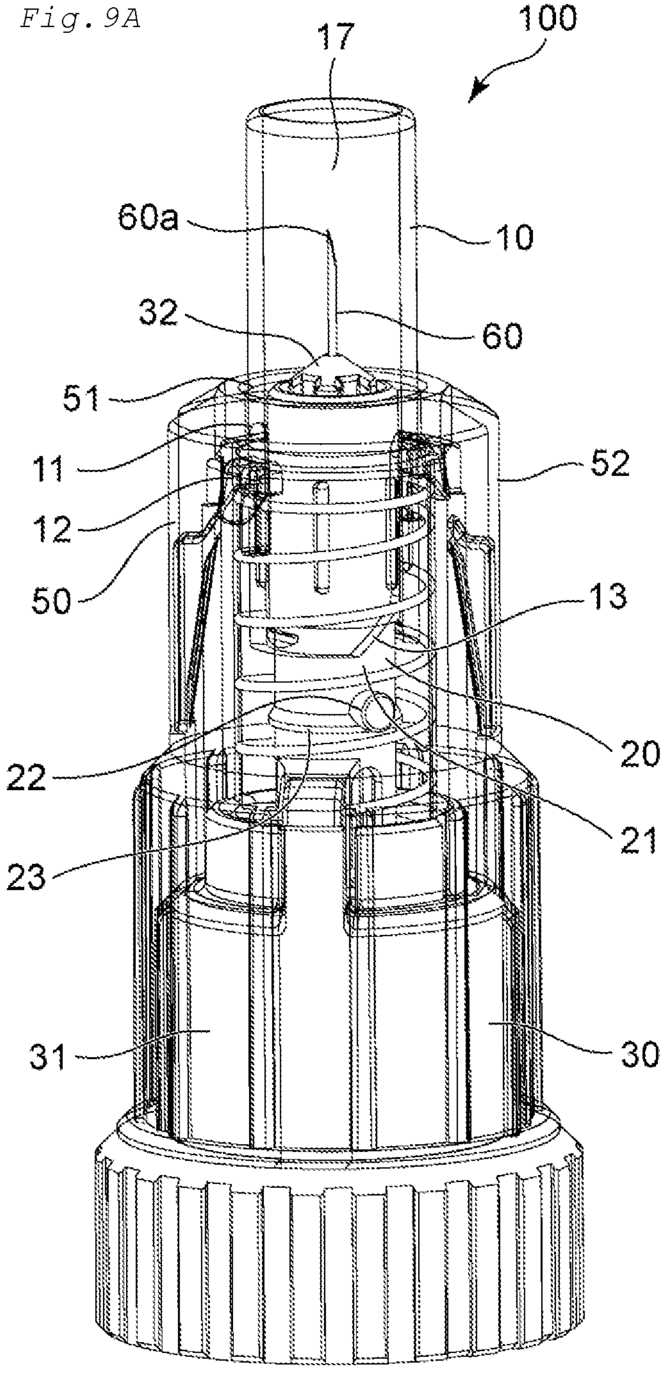
FIG. 9A is a perspective view schematically showing an operation flow (before use) of the assembly according to the embodiment of the present disclosure.
Figure 9B:
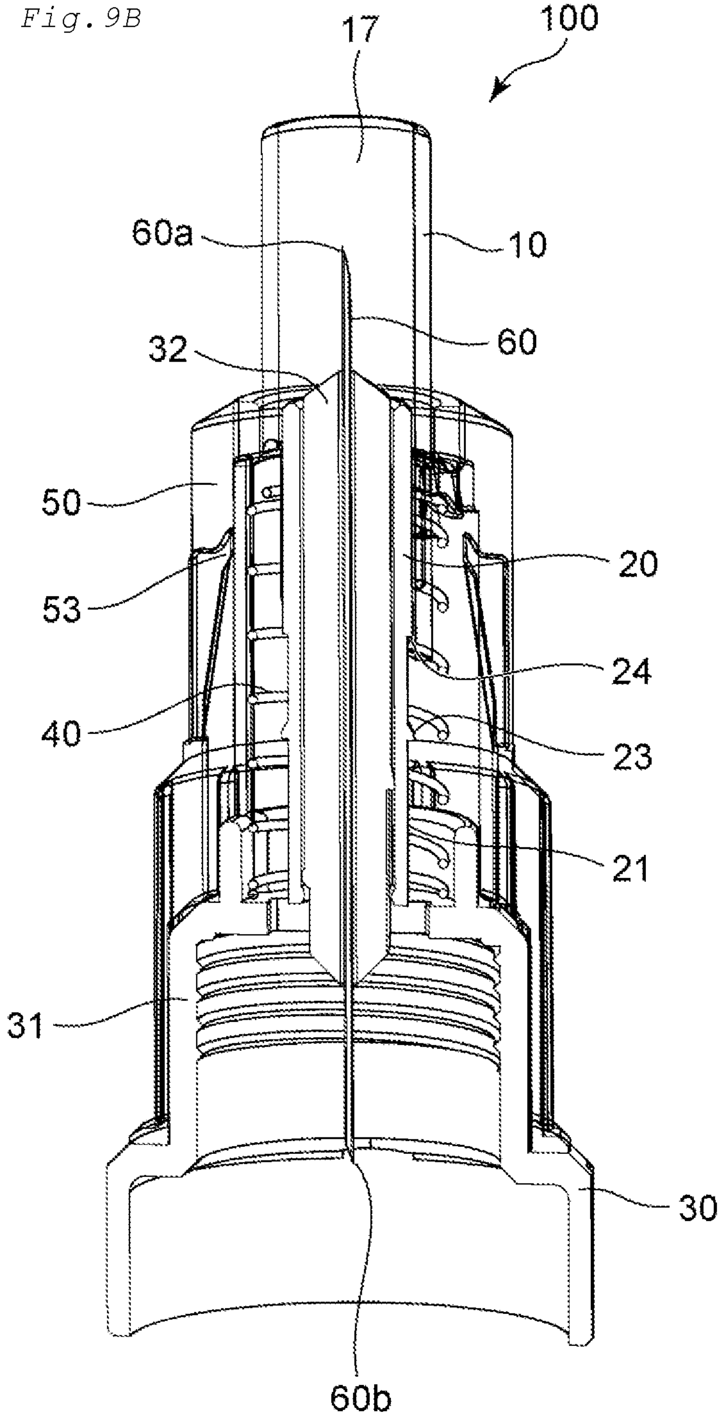
FIG. 9B is a cross-sectional view schematically showing an operation flow (before use) of the assembly according to the embodiment of the present disclosure.

Attachment of Needle Assembly 100 to Pen Injector+Before Movable Needle Cover Portion 10 Moves in One Direction First, the needle assembly 100 according to the embodiment of the present disclosure is attached to a pen injector including a medicinal solution therein (see FIGS. 9A and 9B).

FIG. 9A is a perspective view schematically showing an operation flow (before use) of the assembly according to the embodiment of the present disclosure. FIG. 9B is a cross-sectional view schematically showing an operation flow (before use) of the assembly according to the embodiment of the present disclosure.

Specifically, the inner surface of the base portion 31 of the needle support portion 30 and the outer surface of the pen injector 200 are connected and held, and the non-injection end 60*b* of the hollow needle 60 supported and fixed to the extending portion 32 of the needle support portion 30 is inserted into the pen injector 200 (see also FIG. 1B). As a result, the needle assembly 100 according to the embodiment of the present disclosure can be attached to the pen injector including the medicinal solution therein.

Next, in order to administer the medicinal solution to the body, the overall cover portion 70 attached to cover the integrally combined components (the movable needle cover portion 10, the tubular portion 20, the needle support portion 30 with the hollow needle 60, the biasing portion 40, and the casing 50) is removed. Before the movable needle cover portion 10 after the removal of the overall cover portion 70 moves in one direction, the movable needle cover portion 10 is biased in the opposite direction (pushing-up direction) by the biasing portion 40 arranged between the base portion 31 of the needle support portion 30 and the first needle cover portion projection portion 12 of the movable needle cover portion 10.

Specifically, before the movable needle cover portion 10 moves in one direction, the movable needle cover portion 10 is biased by the biasing portion 40 so as to be positioned at a position where the medicinal solution injection-side end portion 60*a* of the hollow needle 60 does not protrude outward. As a result, it is possible to maintain a state where the medicinal solution injection-side end portion 60*a* of the hollow needle 60 does not protrude outward before the movable needle cover portion 10 moves in one direction after the removal of the overall cover portion 70.

Before the movable needle cover portion 10 moves in one direction, the step portion 24 of the tubular portion 20 and the second needle cover portion projection portion 19 located on the inner side surface 18 of the movable needle cover portion 10 can be locked to each other. Furthermore, the first needle cover portion projection portion 12 of the movable needle cover portion 10 can be locked to the upper surface 56 or the side surface 52 forming the opening portion 51 of the casing 50. Thus, it is possible to suitably avoid detachment of the movable needle cover portion 10 from the casing 50 when the needle assembly 100 is not used (corresponding to before the movable needle cover portion 10 moves in one direction).

From the above, the movable needle cover portion 10 in which detachment from the casing 50 is avoided is biased so as to be positioned at a position where the hollow needle 60 does not protrude outward. As a result, before the movable needle cover portion 10 moves in one direction (corresponding to before the start of puncture), it is possible to suitably suppress detachment of the movable needle cover portion 10 and/or erroneous insertion of the hollow needle 60 into a medical worker or the like due to exposure of the hollow needle 60 to the outside by movement in the pushing-down direction.

Start Moving of Movable Needle Cover Portion 10 in One Direction

Next, a medical worker or a patient starts movement of the movable needle cover portion 10 in one direction (corresponding to the pushing-down direction). In the start stage of the movement, the movable needle cover portion 10, the tubular portion 20, and the biasing portion 40 perform the following operations (see FIGS. 10A and 10B).

Specifically, the movement of the movable needle cover portion 10 in one direction is started in a state where the movable needle cover portion 10 is pressed against the skin of the patient or the like such that the medicinal solution injection-side end portion 60*a* of the hollow needle 60 can protrude outward from the movable needle cover portion 10. In actual operation, the casing 50 is pushed into the skin side of the patient or the like in a state where the movable needle cover portion 10 is pressed against the skin of the patient or the like, and the movement of the movable needle cover portion 10 in one direction is started using the reaction force generated at that time.

As described above, the locked portion 53 of the casing 50 is positioned at a position that is not locked to the first needle cover portion projection portion 12 of the movable needle cover portion 10 before the pushing-down movement (corresponding to before the movement in one direction). That is, before the pushing-down movement of the movable needle cover portion 10, the locked portion 53 of the casing 50 and the first needle cover portion projection portion 12 of the movable needle cover portion 10 have a positional relationship in which they do not face each other, a positional relationship in which they are not coaxial, and/or a positional relationship in which they are not on the same line. Since such a positional relationship is adopted, the first needle cover portion projection portion 12 of the movable needle cover portion 10 is not locked to the locked portion 53 of the casing 50 before the pushing-down movement of the movable needle cover portion 10 (corresponds to before the movement in one direction), so that the movable needle cover portion 10 can be smoothly moved in one direction.

As described above, the biasing portion 40 is arranged between the base portion 31 of the needle support portion 30 and the first needle cover portion projection portion 12 such that one end thereof is in contact with the upper surface of the base portion 31 of the needle support portion 30 and the other end thereof is in contact with the first needle cover portion projection portion 12 of the movable needle cover portion 10. In a case of using a compression coil spring as the biasing portion 40, contraction of the compression coil spring located between the base portion 31 of the needle support portion 30 and the first needle cover portion projection portion 12 starts as the movable needle cover portion 10 starts to move in one direction (pushing-down direction).

In Middle of Movement of Movable Needle Cover Portion 10 in One Direction

After the start of the movement of the movable needle cover portion 10 in one direction, in the middle stage of the movement, the movable needle cover portion 10, the tubular portion 20, and the biasing portion 40 perform the following operations (see FIGS. 10A to 12B).

Figure 10A:
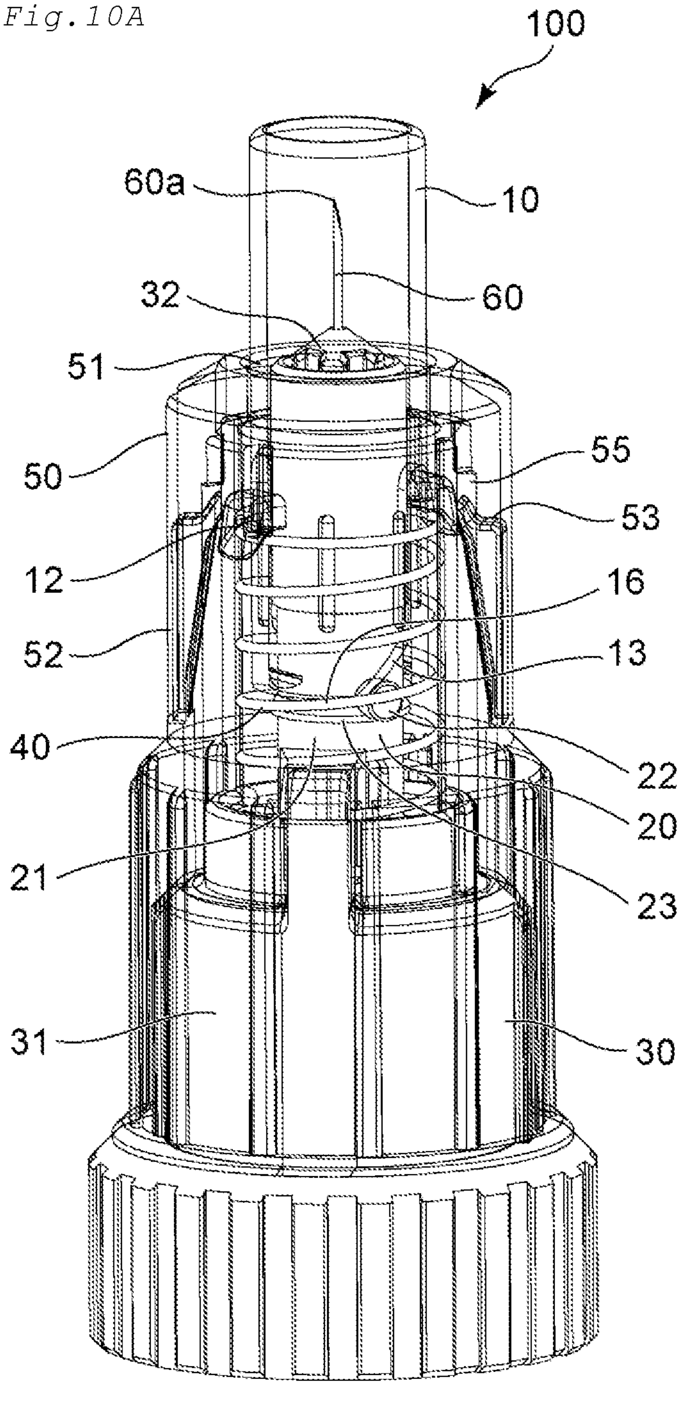
FIG. 10A is a perspective view schematically showing an operation flow (in the middle of movement of the movable needle cover portion in one direction/at the time of abutment of a side surface lower end portion of the movable needle cover portion against a first tubular portion projection portion of the tubular portion) of the assembly according to the embodiment of the present disclosure.
Figure 10B:
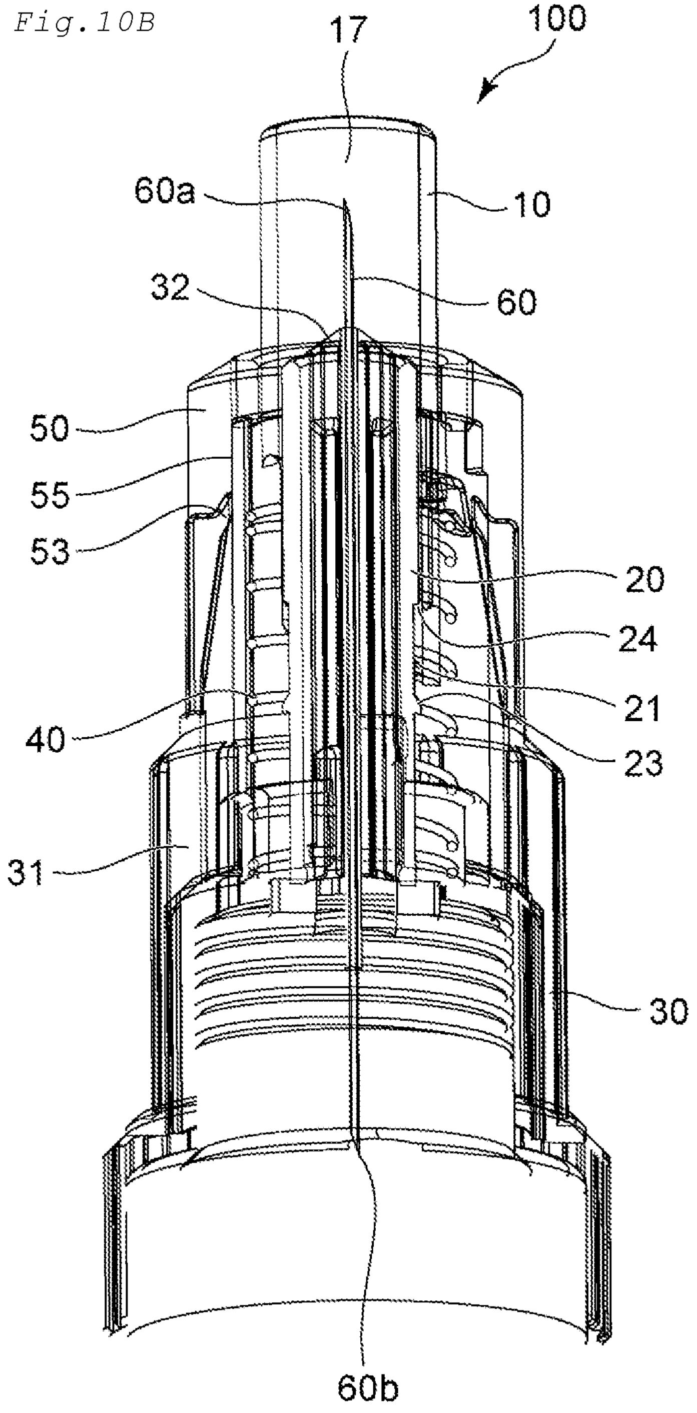
FIG. 10B is a cross-sectional view schematically showing an operation flow (in the middle of the movement of the movable needle cover portion in one direction/at the time of abutment of the side surface lower end portion of the movable needle cover portion against the first tubular portion projection portion of the tubular portion) of the assembly according to the embodiment of the present disclosure.

Specifically, as shown in FIGS. 10A and 10B, in the middle stage of the movement of the movable needle cover portion 10 in one direction, the side surface lower end portion 16 of the movable needle cover portion 10 abuts on the first tubular portion projection portion 22 of the tubular portion 20. At the time of such abutment, as described above, since at least one of the side surface lower end portion 16 of the movable needle cover portion 10 and the first tubular portion projection portion 22 of the tubular portion 20 has the inclined surface, the axial rotational force can be applied to the cover portion 10 while the movable needle cover portion 10 moves in one direction (pushing-down direction).

Figure 11A:
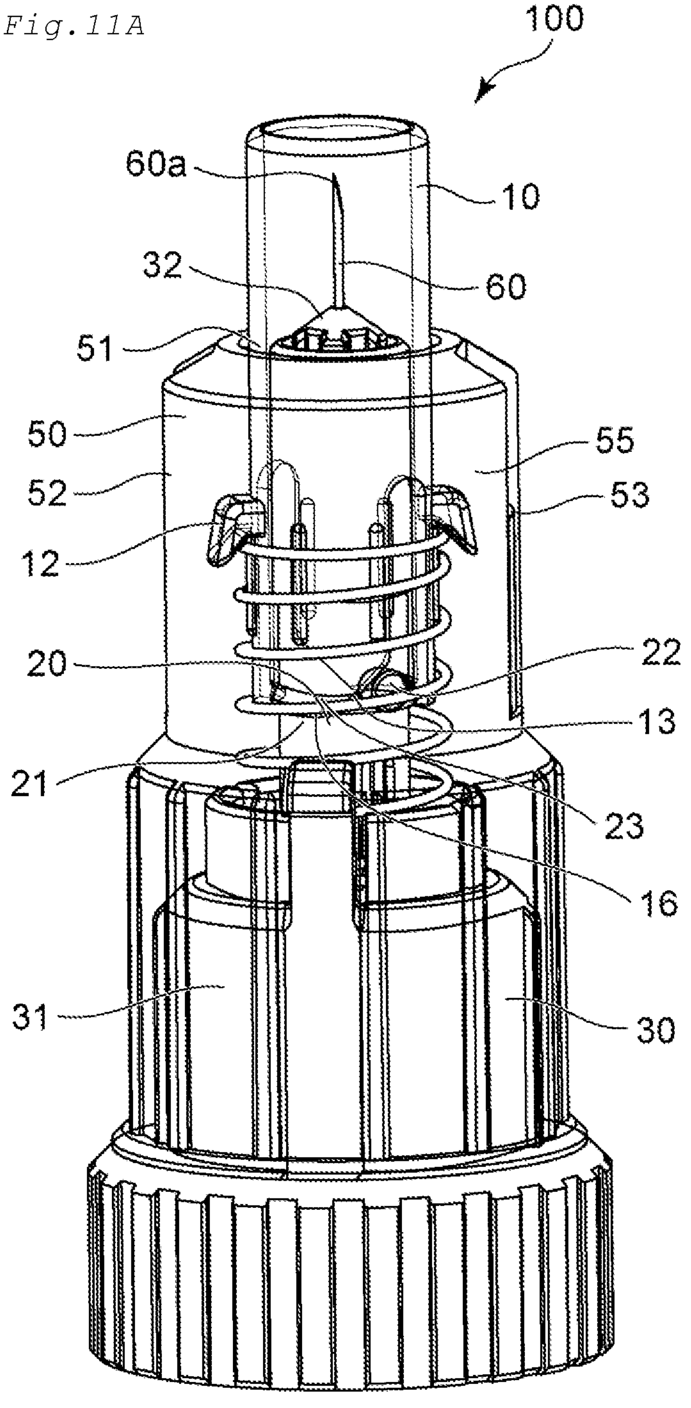
FIG. 11A is a perspective view schematically showing an operation flow (in the middle of the movement of the movable needle cover portion in one direction/at the start of axial rotation of the first tubular portion projection portion of the tubular portion) of the assembly according to the embodiment of the present disclosure.
Figure 11B:
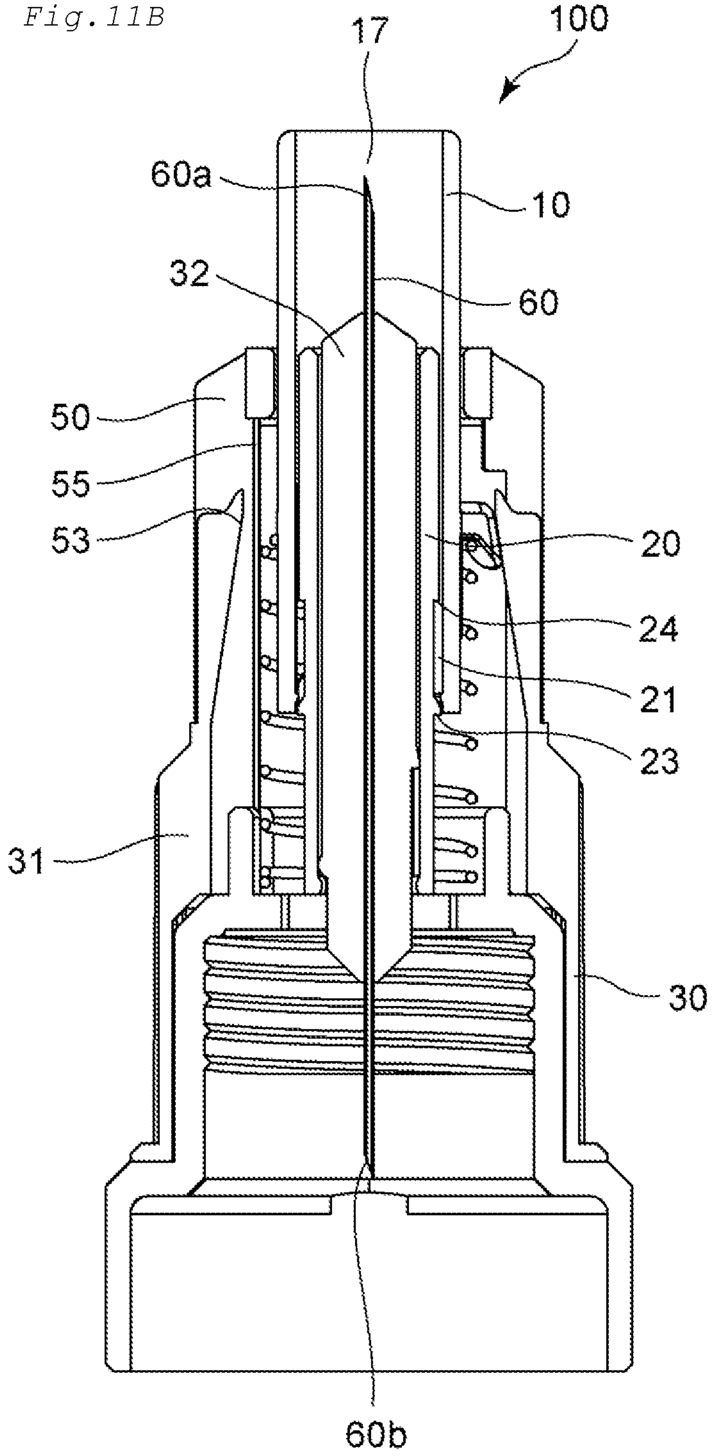
FIG. 11B is a cross-sectional view schematically showing an operation flow (in the middle of the movement of the movable needle cover portion in one direction/at the start of the axial rotation of the first tubular portion projection portion of the tubular portion) of the assembly according to the embodiment of the present disclosure.

As a result, as shown in FIGS. 11A and 11B, the movable needle cover portion 10 to be pushed down can start axial rotation with respect to the tubular portion 20. Note that, in a case where the axial rotation target is the movable needle cover portion 10 alone, in order to suitably apply the axial rotational force to the movable needle cover portion 10, it is preferable that the tubular portion 20, which is a counterpart abutted at the time of axial rotation of the movable needle cover portion 10, is held on the upper surface of the base portion 31 of the needle support portion 30 without axial rotation.

In the middle stage of the movement of the movable needle cover portion 10 in one direction, the compression coil spring as the biasing portion 40 located between the base portion 31 of the needle support portion 30 and the first needle cover portion projection portion 12 further contracts as compared with the start stage of the movement in one direction.

As described above, the movable needle cover portion 10 adopts a configuration including the notch portion 15 continuous with the side surface lower end portion 16 capable of abutting on the first tubular portion projection portion 22. Taking the case where the side surface lower end portion 16 that can abut on the first tubular portion projection portion 22 is the inclined surface 13 as an example, by adopting such a configuration, the movable needle cover portion 10 that has started axial rotation shifts from a "state where the inclined surface 13 and the first tubular portion projection portion 22 directly face each other at the time of abutment" to a "state where the notch portion 15 and the first tubular portion projection portion 22 are positioned substantially coaxially".

Figure 12A:
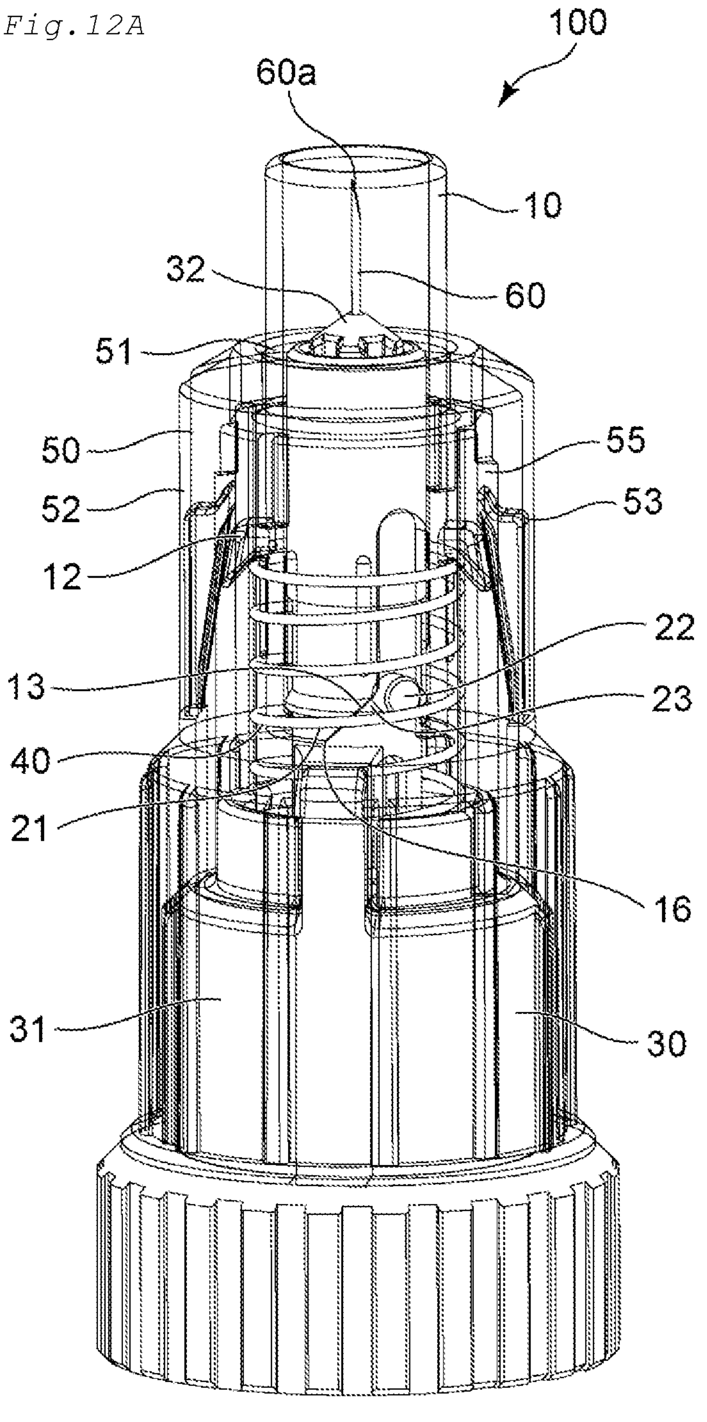
FIG. 12A is a perspective view schematically showing an operation flow (in the middle of the movement of the movable needle cover portion in one direction/at the completion of the axial rotation of the first tubular portion projection portion of the tubular portion) of the assembly according to the embodiment of the present disclosure.
Figure 12B:
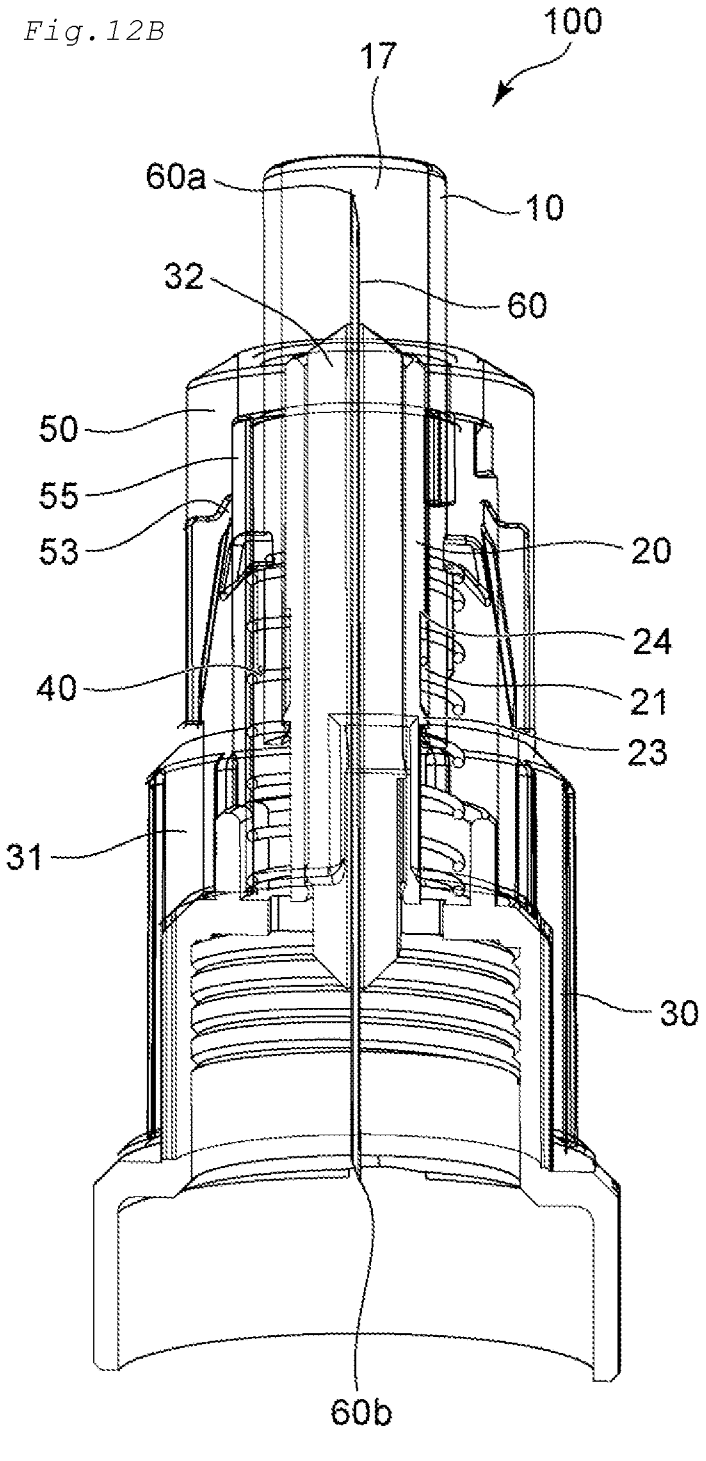
FIG. 12B is a cross-sectional view schematically showing an operation flow (in the middle of the movement of the movable needle cover portion in one direction/at the completion of the axial rotation of the first tubular portion projection portion of the tubular portion) of the assembly according to the embodiment of the present disclosure.

When the shift of such a state is completed, that is, when the movable needle cover portion 10 is in the "state of being located substantially coaxially with the notch portion 15 and the first tubular portion projection portion 22", as shown in FIGS. 12A and 12B, in the embodiment of the present disclosure, the axial rotation of the movable needle cover portion 10 is completed.

In the needle assembly 100 of the present disclosure, the timing at which the axial rotation of the movable needle cover portion 10 is completed is preferably configured to be earlier than the timing at which the hollow needle 60 comes out from the opening portion of the movable needle cover portion 10. As a result, at the timing when the hollow needle 60 comes out, the movable needle cover portion 10 is ready to be moved in the pushing-up direction by the biasing portion 40. Therefore, it is possible to avoid the medicinal solution injection-side end portion 60*a* of the hollow needle 60 from protruding to the outside of the movable needle cover portion 10.

When Movement of Movable Needle Cover Portion 10 in One Direction is Completed After the axial rotation (which may be referred to as after the completion of the axial rotation), since the notch portion 15 and the first tubular portion projection portion 22 are located substantially coaxially, the movable needle cover portion 10 can be further pushed down and moved in one direction without abutting on the first tubular portion projection portion 22 again.

Figure 13A:
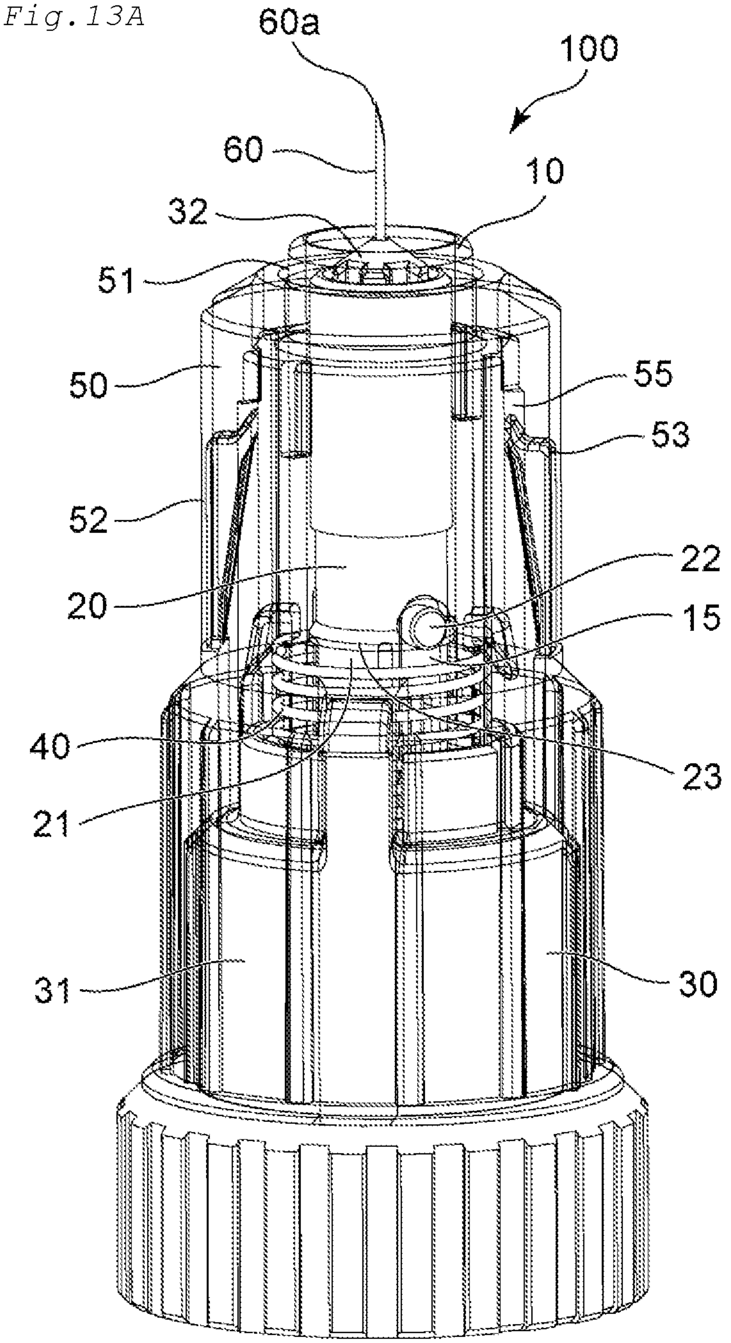
FIG. 13A is a perspective view schematically showing an operation flow (at the completion of the movement of the movable needle cover portion in one direction) of the assembly according to the embodiment of the present disclosure.
Figure 13B:
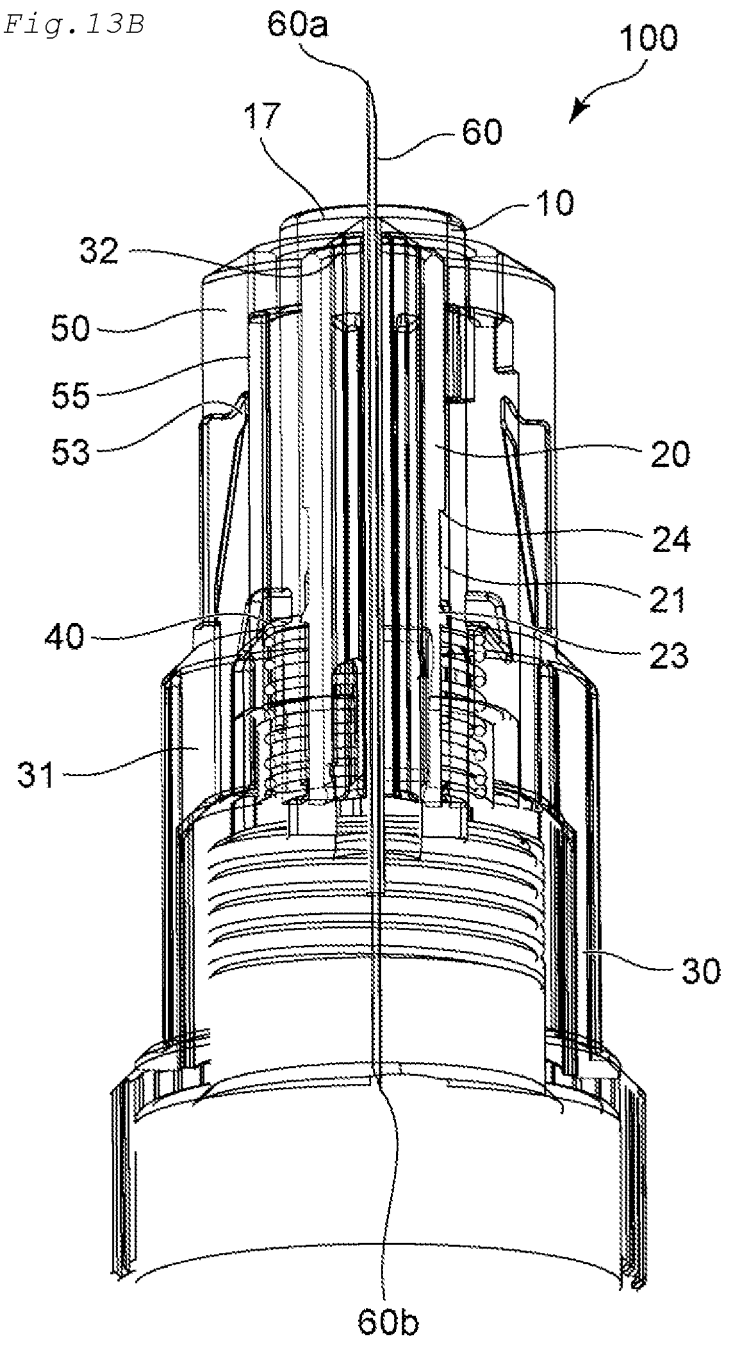
FIG. 13B is a cross-sectional view schematically showing an operation flow (at the completion of the movement of the movable needle cover portion in one direction) of the assembly according to the embodiment of the present disclosure.

When the further pushing-down movement of the movable needle cover portion 10 in one direction is continued, the side surface lower end portion 16 of the movable needle cover portion 10 can finally abut on the upper surface of the base portion 31 of the needle support portion 30. As a result, the movement of the movable needle cover portion 10 (pushing-down movement) in one direction is completed as shown in FIGS. 13A and 13B. In the embodiment of the present disclosure, when the movement in one direction is completed, the medicinal solution injection-side end portion 60*a* of the hollow needle 60 attached to the needle support portion 30 can suitably protrude to the outside of the movable needle cover portion 10.

In the completion stage of the movement of the movable needle cover portion 10 in one direction, the compression coil spring as the biasing portion 40 located between the base portion 31 of the needle support portion 30 and the first needle cover portion projection portion 12 further contracts as compared with the middle stage of the movement in one direction.

Medicinal Solution is Administered

When the movement of the movable needle cover portion 10 in one direction is completed, the medicinal solution is administered into the body (see FIGS. 13A and 13B).

As described above, the needle assembly 100 according to the embodiment of the present disclosure is used in a state where the movable needle cover portion 10 is pressed against the skin of a patient or the like. When the medicinal solution injection-side end portion 60*a* protrudes to the outside of the movable needle cover portion 10 in such a state, the hollow needle 60 including the medicinal solution injection-side end portion 60*a* can puncture the body through the skin of the patient or the like. In such a puncture state, the medicinal solution is administered from the pen injector including the medicinal solution therein into the body of the patient or the like via the hollow needle 60.

Start Moving of Movable Needle Cover Portion 10 in Opposite Direction (after Completion of Medicinal Solution Administration)

When the administration of the predetermined amount of the medicinal solution is completed, the puncture state of the hollow needle 60 on the skin of the patient or the like is released, and the movable needle cover portion 10 is separated from the skin.

("Automatic" Accommodating of Medicinal Solution Injection-Side End Portion 60*a*)

In the previous stage of separating the movable needle cover portion 10 from the skin of the patient or the like, the compression coil spring as the biasing portion 40 is contracted as described above. When the biasing portion 40 is in the contracted state, the movable needle cover portion 10 can be biased by the biasing portion 40. Then, when the movable needle cover portion 10 is separated from the skin of the patient or the like, a force to expand acts on the compression coil spring as the biasing portion 40 that has contracted once. In addition, the base portion 31 of the needle support portion 30 is in a held state, that is, in a non-moving state.

Figure 14A:
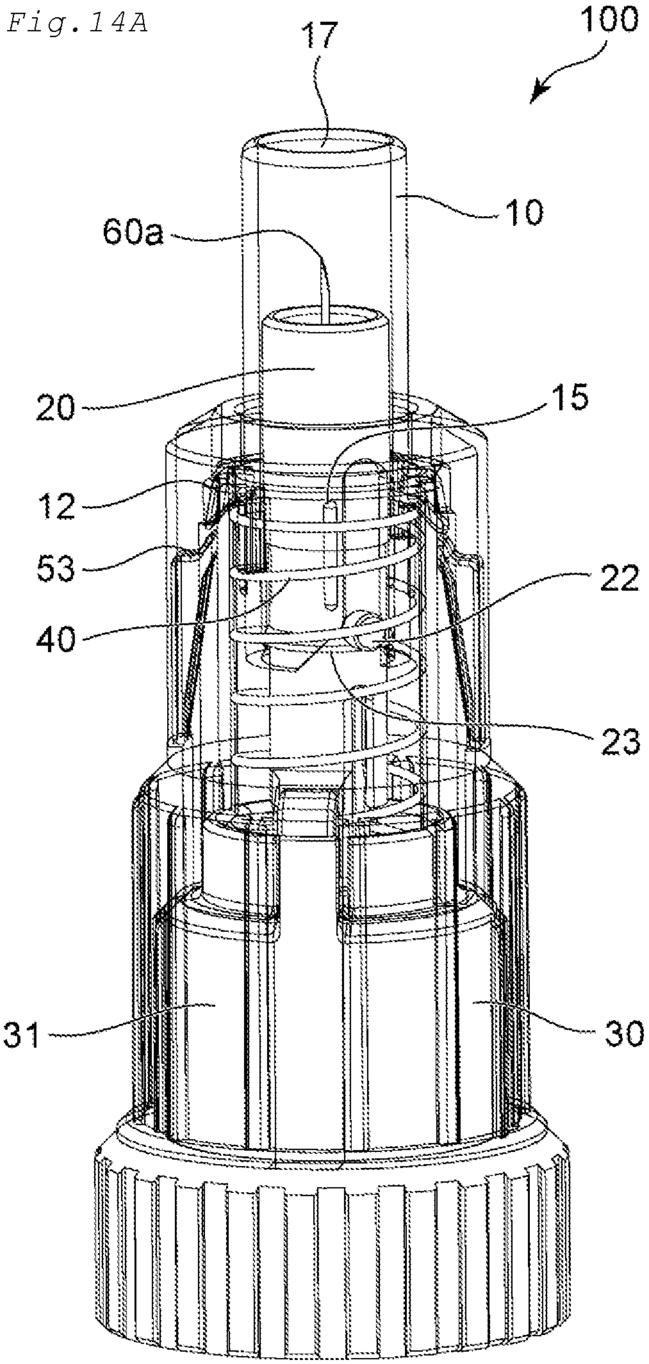
FIG. 14A is a perspective view schematically showing an operation flow (at the completion of the movement of the movable needle cover portion in an opposite direction) of the assembly according to the embodiment of the present disclosure.
Figure 14B:
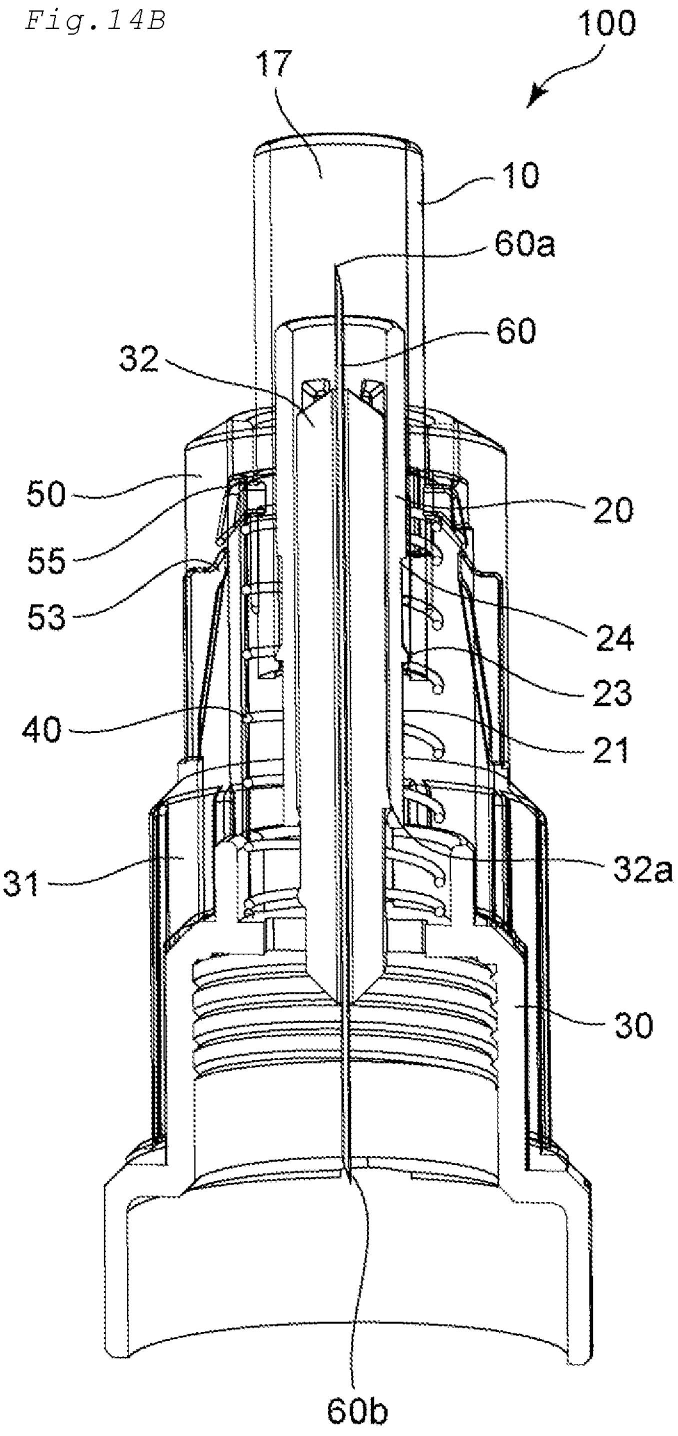
FIG. 14B is a cross-sectional view schematically showing an operation flow (at the completion of the movement of the movable needle cover portion in the opposite direction) of the assembly according to the embodiment of the present disclosure.

From the above, the movable needle cover portion 10 is biased in the opposite direction (pushing-up direction) by the force to expand acting on the biasing portion 40, whereby the movable needle cover portion 10 can be moved in the opposite direction (pushing-up direction). As a result, as shown in FIGS. 14A and 14B, the medicinal solution injection-side end portion 60*a* of the needle 60 that has once protruded outward from the movable needle cover portion 10 can be "automatically" accommodated inside the movable needle cover portion 10.

As described above, the shape of the first needle cover portion projection portion 12 is a shape that is not locked to the locked portion 53 of the casing 50 and can pass over the locked portion 53 when the movable needle cover portion 10 moves in the pushing-up direction (opposite direction). Therefore, the movable needle cover portion 10 can smoothly move in the pushing-up direction in a state where the locking between the first needle cover portion projection portion 12 and the locked portion 53 of the casing 50 is avoided.

(Prevention of "Re-Moving" of Movable Needle Cover Portion 10 in One Direction (Pushing-Down Direction))

When the movable needle cover portion 10 further moves in the pushing-up direction, the first needle cover portion projection portion 12 gets over the locked portion 53 of the casing 50. As described above, the movable needle cover portion 10 is configured such that the first needle cover portion projection portion 12 can be locked to the locked portion 53 of the casing 50 when moving in the pushing-down direction (one direction).

Therefore, once the first needle cover portion projection portion 12 gets over the locked portion 53 of the casing 50, even if a force of re-moving in the pushing-down direction (one direction) acts on the movable needle cover portion 10, the re-moving of the movable needle cover portion 10 in the pushing-down direction (one direction) can be suitably suppressed by the locking between the first needle cover portion projection portion 12 and the locked portion 53.

As an example, the locked portion 53 may correspond to the lower edge portion of the profile portion defining the second opening portion 55 formed in the side surface of the casing 50. In this case, a part of the first needle cover portion projection portion 12 described later protrudes outward through the second opening portion 55, and then a part of the protruding first needle cover portion projection portion 12 can be locked to the locked portion 53 (corresponding to the lower edge portion of the contour portion forming the second opening portion 55).

When the slit 54 is formed along the longitudinal direction of the side surface 52 from both ends of the locked portion 53 (corresponding to the lower edge portion of the contour portion forming the second opening portion 55), flexibility can be provided to the locked portion 53. As a result, it is possible to smoothly lock a part of the first needle cover portion projection portion 12 protruding outward through the second opening portion 55 to the locked portion 53 as compared with the case where the slit 54 is not formed. From another point of view, the presence of the slit 54 is also advantageous in that the first needle cover portion projection portion 12 easily gets over the locked portion 53 of the casing 50 when the movable needle cover portion 10 further moves in the pushing-up direction.

(Prevention of "Detachment" of Movable Needle Cover Portion 10 from Casing 50)

Figure 3:
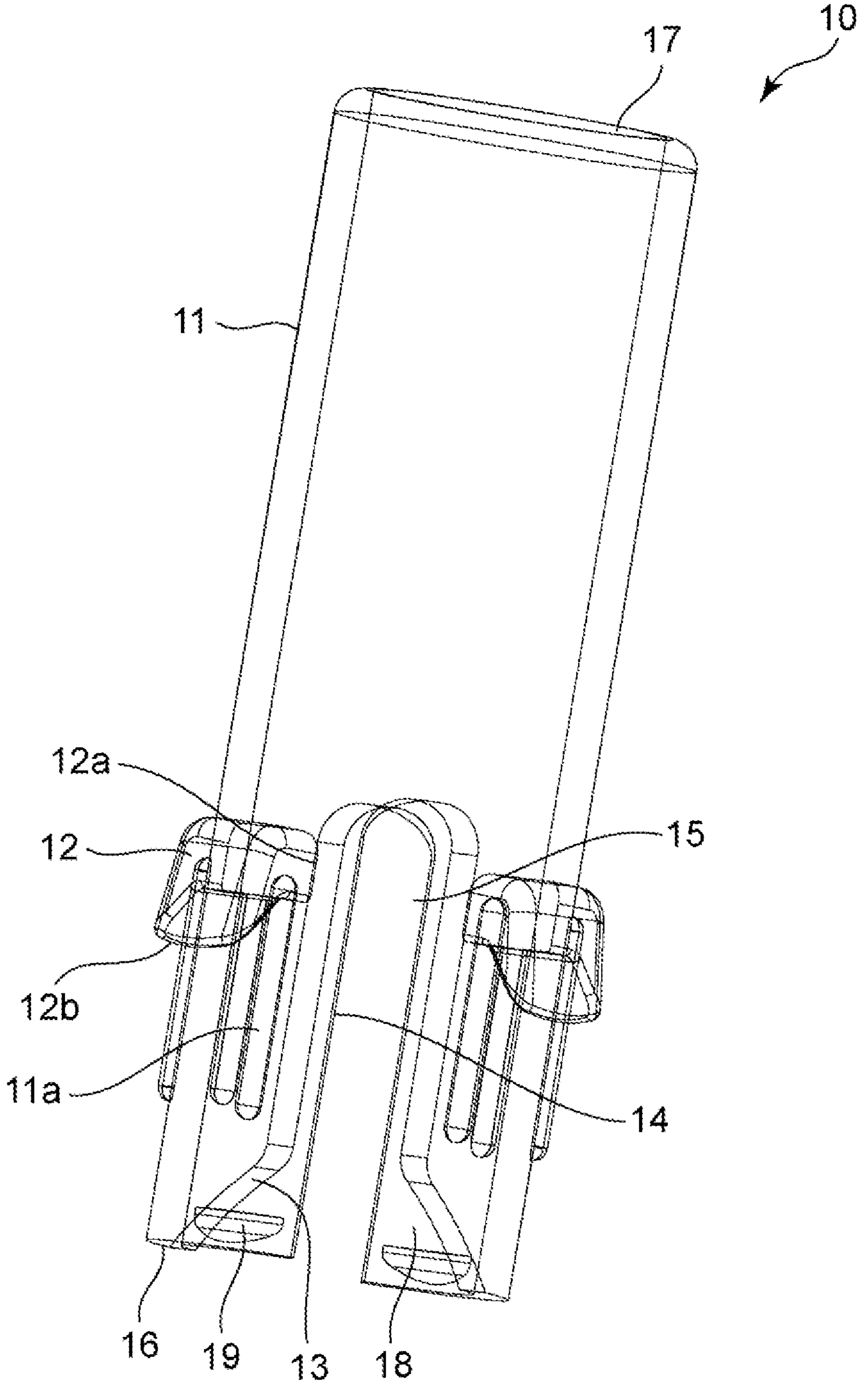
FIG. 3 is a perspective view schematically showing a movable needle cover portion.
Figure 4A:
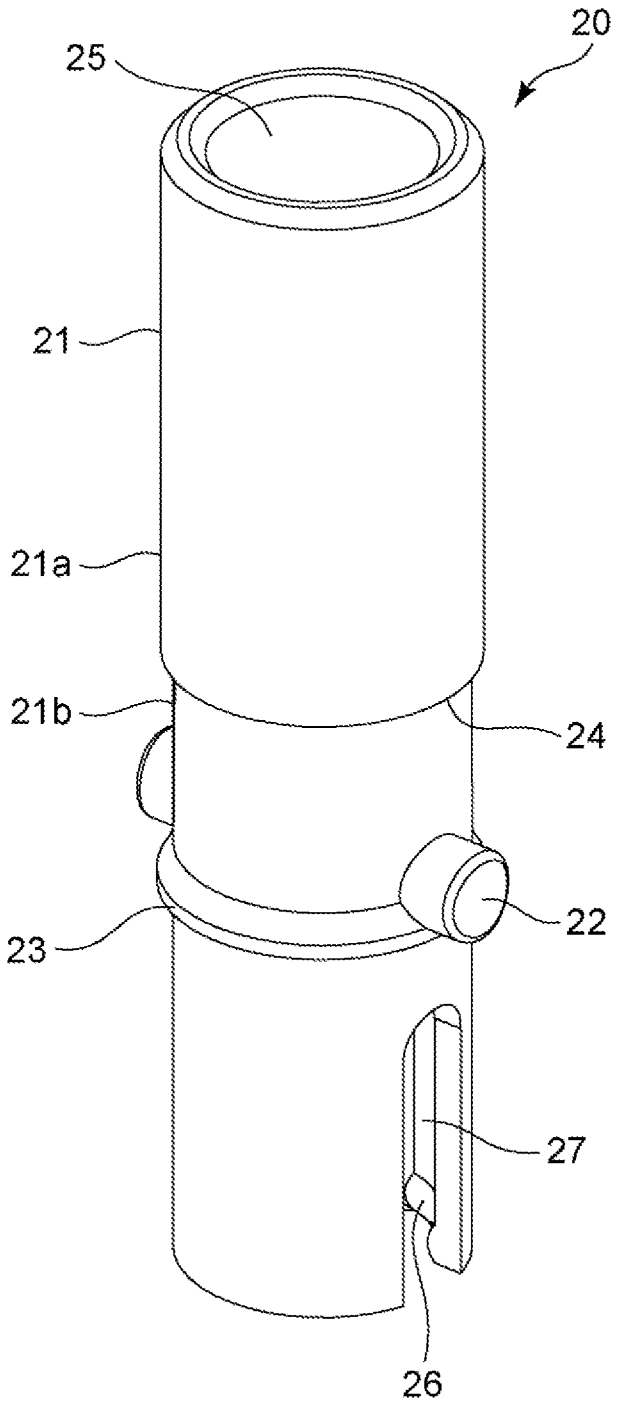
FIG. 4A is a perspective view schematically showing a tubular portion.
Figure 4B:
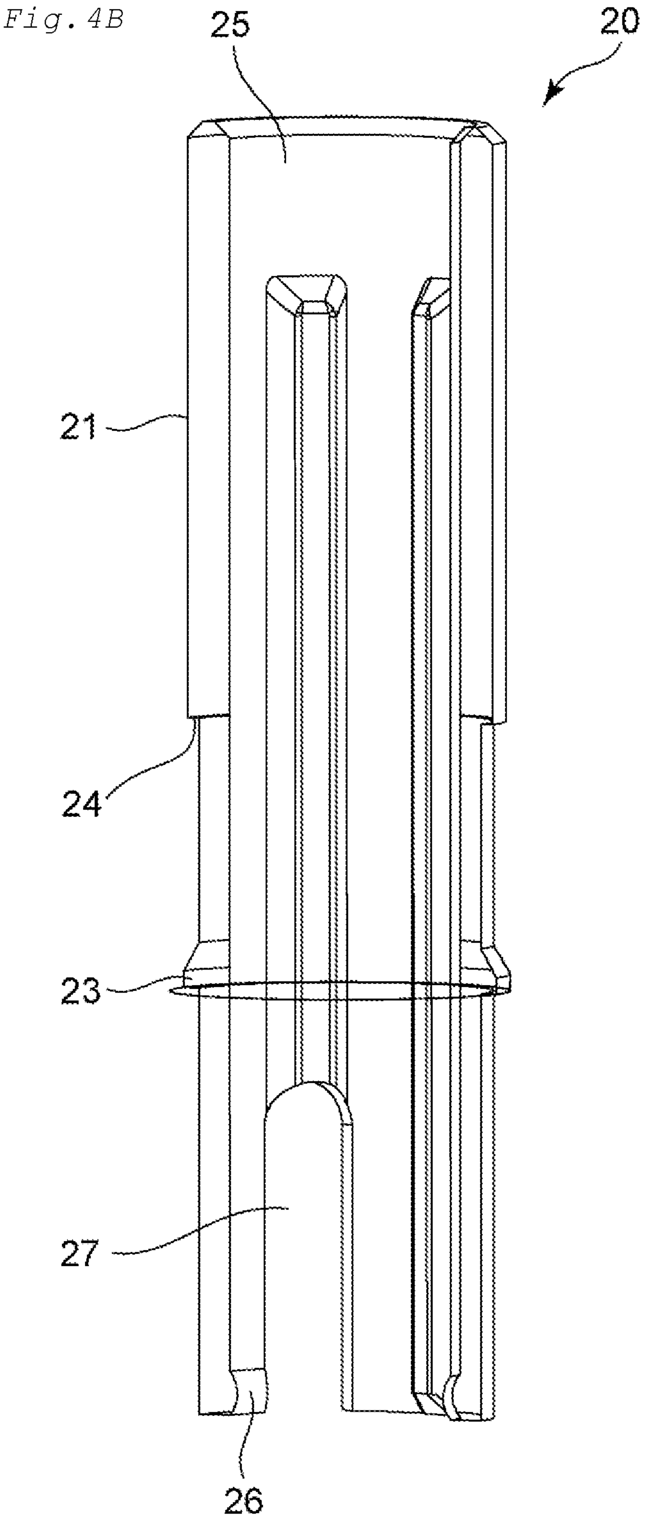
FIG. 4B is a cross-sectional view schematically showing the tubular portion.

As described above, the second needle cover portion projection portion 19 located inside the movable needle cover portion 10 can be locked to the step portion 24 formed on the outer side surface 21 of the tubular portion 20 (see also FIGS. 3, 4A, and 4B). Furthermore, the first needle cover portion projection portion 12 of the movable needle cover portion 10 can be locked to the upper surface 56 or the side surface 52 forming the opening portion 51 of the casing 50.

By the locking of both, it is possible to suitably avoid detachment of the movable needle cover portion 10 from the casing 50 after completion of movement of the movable needle cover portion 10 in the opposite direction (pushing-up direction). Therefore, it is possible to suitably avoid the hollow needle 60 from being exposed to the outside when the use of the needle assembly 100 is completed. Accordingly, safety at the time of completion of use of the needle assembly 100 can also be suitably ensured.

(Use of Tubular Portion as Marker Portion)

As already described above, description is made in a simplified manner in order to avoid overlapping of the contents, the configuration in which the tubular portion 20 is integrally movable with the movable needle cover portion 10 after the axial rotation enables the tubular portion 20 to move in the opposite direction (pushing-up direction) in addition to the movable needle cover portion 10 after the axial rotation.

Such integral movement can be realized by a configuration in which the second needle cover portion projection portion 19 is locked to the second tubular portion projection portion 23 of the tubular portion 20 when the movable needle cover portion 10 moves in the pushing-up direction. Furthermore, as described above, since the re-moving of the movable needle cover portion 10, which has completed the movement in the opposite direction, in one direction (pushing-down direction) is suppressed, the tubular portion 20 that integrally moves together with the movable needle cover portion 10 can also be suppressed from re-moving in one direction (pushing-down direction).

At this time, when the movement of the movable needle cover portion 10 in the opposite direction (pushing-up direction) is completed, if a part of the tubular portion 20 integrally movable with the movable needle cover portion 10 can protrude from at least the opening portion 51 of the casing 50, the protruding state is fixedly maintained. Therefore, the tubular portion 20 in which the protruding state is fixedly maintained can be used as a determination element for determining whether the hollow needle 60 is used.

In particular, when the movable needle cover portion 10 is transparent or translucent, and the tubular portion 20 is the colored marker portion, the colored tubular portion 20 maintained protruding from the opening portion 51 of the casing 50 can be visually recognized from the outside through the movable needle cover portion 10. Therefore, it is possible to easily determine that the hollow needle 60 has been used.

Although the embodiment of the present disclosure has been described above, it is merely exemplary within the scope of application of the present disclosure. Accordingly, those skilled in the art will readily appreciate that the present disclosure is not limited thereto and that various modifications may be made.

Note that the embodiment of the present invention as described above includes the following preferred aspects.

First Aspect:

A needle assembly comprising:

a needle support portion in which a hollow needle through which a medicinal solution can flow is supported;

a movable needle cover portion that is movable in an opening portion of a casing such that an injection-side end portion of the medicinal solution of the needle protrudes outward in use;

a tubular portion arranged on the needle support portion and partially abuttable with the movable needle cover portion; and a biasing portion configured to bias the movable needle cover portion in a direction opposite to one direction along with movement of the movable needle cover portion in the one direction, the needle support portion, the movable needle cover portion, the tubular portion, and the biasing portion being each configured to be at least partially accommodated in the casing having the opening portion, wherein at least the movable needle cover portion abuts on the tubular portion by the movement of the movable needle cover portion in the one direction to axially rotate from a predetermined position before movement to another position, so that the movable needle cover portion after the axial rotation is movable in the opposite direction by the biasing portion, and wherein the movable needle cover portion after the axial rotation, which has completed the movement in the opposite direction, can be locked to the casing.

Second Aspect:

The needle assembly in the first aspect, wherein the tubular portion is integrally movable with the movable needle cover portion after the axial rotation.

Third Aspect:

The needle assembly in the second aspect, wherein when the movement of the movable needle cover portion in the opposite direction is completed, a part of the tubular portion integrally movable with the movable needle cover portion can protrude from at least the opening portion of the casing.

Fourth Aspect:

The needle assembly in any one of the first to third aspects, wherein the movable needle cover portion is transparent or translucent, and the tubular portion is a colored marker portion for determining whether the needle has been used.

Fifth Aspect:

The needle assembly in any one of the first to fourth aspects, wherein the movable needle cover portion has a substantially cylindrical shape, and the tubular portion having a first tubular portion projection portion on an outer side surface is positioned in an inner region of the movable needle cover portion having the cylindrical shape, and wherein at least one of a side surface lower end portion of the movable needle cover portion and the first tubular portion projection portion has an inclined surface that can abut on each other, and the side surface lower end portion of the movable needle cover portion abuts on the first tubular portion projection portion along with the movement of the movable needle cover portion in the one direction, whereby the movable needle cover portion can axially rotate.

Sixth Aspect:

The needle assembly in the fifth aspect, wherein only the side surface lower end portion of the movable needle cover portion has the inclined surface, and the first tubular portion projection portion has a substantially circular shape in a cross-sectional view or a side view.

Seventh Aspect:

The needle assembly in the fifth aspect or sixth aspect, wherein the movable needle cover portion includes a notch portion continuous with the side surface lower end portion abutting on the first tubular portion projection portion, and wherein after the axial rotation of the movable needle cover portion, the notch portion and the first tubular portion projection portion can be positioned substantially coaxially.

Eighth Aspect:

The needle assembly in the seventh aspect, wherein the notch portion enables the movable needle cover portion after the axial rotation to be further pushed down and moved in the one direction without abutting on the first tubular portion projection portion.

Ninth Aspect:

The needle assembly in any one of the first to eighth aspects, wherein the movable needle cover portion includes a first needle cover portion projection portion locally formed on an outer side surface, and the biasing portion is arranged between the needle support portion and the first needle cover portion projection portion.

Tenth Aspect:

The needle assembly in the ninth aspect, wherein the movable needle cover portion after the axial rotation, which has been pushed down and moved in the one direction, is movable in the opposite direction via the first needle cover portion projection portion by the biasing portion.

Eleventh Aspect:

The needle assembly in the ninth aspect or tenth aspect, wherein the first needle cover portion projection portion of the movable needle cover portion after the axial rotation can be locked to a locked portion formed on a side surface of the casing.

Twelfth Aspect:

The needle assembly in any one of the ninth to eleventh aspects, wherein the first needle cover portion projection portion has a wing shape.

Thirteenth Aspect:

The needle assembly in any one of the fifth to twelfth aspects, wherein the tubular portion further includes a second tubular portion projection portion different from the first tubular portion projection portion on the outer side surface, the movable needle cover portion further includes a second needle cover portion projection portion on an inner side surface, and the second needle cover portion projection portion can be locked to the second tubular portion projection portion when the movable needle cover portion after the axial rotation moves in the opposite direction.

Fourteenth Aspect:

The needle assembly in any one of the first to thirteenth aspects, wherein the needle assembly is replaceably attached to a pen injector including the medicinal solution therein.

Fifteenth Aspect:

The needle assembly in any one of the first to fourteenth aspects, wherein the needle support portion includes a base portion, the base portion being capable of accommodating therein a non-injection-side end portion of the needle opposite to the injection-side end portion of the medicinal solution.

Sixteenth Aspect:

The needle assembly in the fifteenth aspect, wherein the needle support portion further includes an extending portion having the needle fixedly supported on the base portion therein, and the extending portion of the needle support portion is movable inside the movable needle cover portion.

INDUSTRIAL APPLICABILITY

The needle assembly according to the embodiment of the present disclosure can be used by being replaceably attached to a pen injector including a medicinal solution therein.

CROSS-REFERENCE TO RELATED APPLICATIONS

The present application claims priority under the Paris Convention to Japanese Patent Application No. 2021 061217 (filing date: Mar. 31, 2021, Title of the Invention: "NEEDLE ASSEMBLY"). The entire contents disclosed in the application are incorporated herein by this reference.

EXPLANATION OF REFERENCES

200 pen injector including medicinal solution therein
100 needle assembly
70 overall cover portion
60 hollow needle
60*a* injection-side end portion of needle
60*b* non-injection-side end portion of needle
50 casing
51 opening portion (first opening portion)
52 side surface
52*a* inner side surface of casing
52*b* outer side surface of casing
53 locked portion
53*a* distal end side of locked portion
53*b* central region of locked portion
54 slit
55 second opening portion
56 upper surface
57 slope surface
58 rib portion
40 biasing portion
30 needle support portion
31 base portion
31*a* upper surface of base portion
31*a* bank portion
31*b* locking portion engageable with locked portion (casing side-surface opening portion) of casing
31*c* rib portion
32 extending portion
32*a* first needle support portion protrusion portion
32*b* convex portion
32*c* second needle support portion protrusion portion
33 concave portion
20 tubular portion
21 outer side surface
21*a* first outer side surface
21*b* second outer side surface
22 first tubular portion projection portion
23 second tubular portion projection portion
24 step portion
25 inner region
26 third tubular portion projection portion
27 slit
10 movable needle cover portion
11 outer side surface
11*a* third needle cover portion projection portion
12 first needle cover portion projection portion
12*a* one end of needle cover portion projection portion
12*b* other end of needle cover portion projection portion
13 inclined surface
14 part of side surface lower end portion having concave shape
15 notch portion
16 side surface lower end portion
17 inner region
18 inner side surface
19 second needle cover portion projection portion

What is claimed is:

1. A needle assembly comprising:

a needle support portion in which a hollow needle through which a medicinal solution is configured to flow is supported;

a movable needle cover portion that is movable in an opening portion of a casing such that an injection-side end portion of the medicinal solution of the needle protrudes outward in use;

a tubular portion arranged on the needle support portion and partially abuttable with the movable needle cover portion; and a biasing portion configured to bias the movable needle cover portion in a direction opposite to one direction along with movement of the movable needle cover portion in the one direction, the needle support portion, the movable needle cover portion, the tubular portion, and the biasing portion each configured to be at least partially accommodated in the casing having the opening portion, wherein at least the movable needle cover portion abuts on the tubular portion by the movement of the movable needle cover portion in the one direction to axially rotate from a predetermined position before movement to another position, so that the movable needle cover portion after the axial rotation is movable in the opposite direction by the biasing portion, wherein the movable needle cover portion after the axial rotation, which has completed the movement in the opposite direction, is locked to the casing, wherein the movable needle cover portion has a substantially cylindrical shape, and the tubular portion having a first tubular projection portion on an outer side surface is positioned in an inner region of the movable needle cover portion having the cylindrical shape, wherein at least one of a side surface lower end portion of the movable needle cover portion and the first tubular projection portion has an inclined surface abuttable on each other, and the side surface lower end portion of the movable needle cover portion abuts on the first tubular projection portion along with the movement of the movable needle cover portion in the one direction, whereby the movable needle cover portion axially rotates, and wherein the first tubular projection portion extends in a direction substantially perpendicular to an axial direction of the tubular portion.

2. The needle assembly according to claim 1, wherein the tubular portion is integrally movable with the movable needle cover portion after the axial rotation.

3. The needle assembly according to claim 2, wherein when the movement of the movable needle cover portion in the opposite direction is completed, a part of the tubular portion integrally movable with the movable needle cover portion protrudes from at least the opening portion of the casing.

4. The needle assembly according to claim 1, wherein the movable needle cover portion is transparent or translucent, and the tubular portion is a colored marker portion for determining whether the needle has been used.

5. The needle assembly according to claim 1, wherein only the side surface lower end portion of the movable needle cover portion has the inclined surface, and the first tubular projection portion has a substantially circular shape in a cross-sectional view or a side view.

6. The needle assembly according to claim 1, wherein the movable needle cover portion includes a notch portion continuous with the side surface lower end portion abutting on the first tubular projection portion, and wherein after the axial rotation of the movable needle cover portion, the notch portion and the first tubular projection portion is positioned substantially coaxially.

7. The needle assembly according to claim 6, wherein the notch portion enables the movable needle cover portion after the axial rotation to be further pushed down and moved in the one direction without abutting on the first tubular projection portion.

8. The needle assembly according to claim 1, wherein the movable needle cover portion includes a first needle cover projection portion locally formed on an outer side surface, and the biasing portion is arranged between the needle support portion and the first needle cover projection portion.

9. The needle assembly according to claim 8, wherein the movable needle cover portion after the axial rotation, which has been pushed down and moved in the one direction, is movable in the opposite direction via the first needle cover projection portion by the biasing portion.

10. The needle assembly according to claim 8, wherein the first needle cover projection portion of the movable needle cover portion after the axial rotation is locked to a locked portion formed on a side surface of the casing.

11. The needle assembly according to claim 8, wherein the first needle cover projection portion has a wing shape.

12. The needle assembly according to claim 1, wherein the tubular portion further includes a second tubular projection portion different from the first tubular projection portion on the outer side surface, the movable needle cover portion further includes a second needle cover projection portion on an inner side surface, and the second needle cover projection portion is locked to the second tubular projection portion when the movable needle cover portion after the axial rotation moves in the opposite direction.

13. The needle assembly according to claim 1, wherein the needle assembly is replaceably attached to a pen injector including the medicinal solution therein.

14. The needle assembly according to claim 1, wherein the needle support portion includes a base portion, the base portion being capable of accommodating therein a non-injection-side end portion of the needle opposite to the injection-side end portion of the medicinal solution.

15. The needle assembly according to claim 14, wherein the needle support portion further includes an extending portion having the needle fixedly supported on the base portion therein, and the extending portion of the needle support portion is movable inside the movable needle cover portion.

* * * * *